United States Patent
Rehkemper et al.

(10) Patent No.: US 7,621,687 B1
(45) Date of Patent: Nov. 24, 2009

(54) SELF-CONTAINED ORAL CLEANING DEVICE

(75) Inventors: Steven Rehkemper, Chicago, IL (US); Jeffrey Rehkemper, Chicago, IL (US); Al Giudice, Glenview, IL (US)

(73) Assignee: Rehco, LLC, Chicago, IL (US)

(*) Notice: Subject to any disclaimer, the term of this patent is extended or adjusted under 35 U.S.C. 154(b) by 354 days.

(21) Appl. No.: 11/178,702

(22) Filed: Jul. 11, 2005

Related U.S. Application Data

(63) Continuation-in-part of application No. 10/772,060, filed on Feb. 3, 2004, now abandoned, which is a continuation-in-part of application No. 10/315,730, filed on Dec. 10, 2002, now Pat. No. 6,689,078, which is a continuation-in-part of application No. 10/233,687, filed on Sep. 4, 2002, now Pat. No. 6,622,333, application No. 11/178,702, which is a continuation-in-part of application No. 10/987,339, filed on Nov. 12, 2004, now Pat. No. 7,140,373, which is a continuation-in-part of application No. 10/886,235, filed on Jul. 7, 2004, now Pat. No. 7,055,531.

(60) Provisional application No. 60/582,777, filed on Jun. 25, 2004.

(51) Int. Cl.
*A46B 11/02* (2006.01)

(52) U.S. Cl. .................... 401/188 R; 401/270; 132/322

(58) Field of Classification Search .............. 401/188 R, 401/270, 272, 273, 278, 279; 433/80, 84, 433/85; 132/322, 323, 324
See application file for complete search history.

(56) References Cited

U.S. PATENT DOCUMENTS

| | | | |
|---|---|---|---|
| 3,195,537 A * | 7/1965 | Blasi | 601/114 |
| 5,208,933 A * | 5/1993 | Lustig et al. | 15/22.1 |
| 5,321,866 A * | 6/1994 | Klupt | 15/22.1 |
| 6,434,773 B1 * | 8/2002 | Kuo | 15/22.1 |

* cited by examiner

*Primary Examiner*—David J Walczak
(74) *Attorney, Agent, or Firm*—Adam K. Sacharoff; Much Shelist

(57) ABSTRACT

An oral cleaning device includes a reservoir with a pump attached to the reservoir, the operation of the pump increases pressure within the reservoir such that liquid contained in the reservoir becomes pressurized. A first mechanism for controlling the flow of pressurized liquid from exiting the reservoir. A mid section attached between a neck portion and the reservoir. A head attached to the neck portion and having an outlet for expelling pressurized liquid contained in the reservoir and further having a movable section rotatably connected thereto. A pathway for allowing pressurized liquid exiting the upper aperture to travel to the outlet in the head. An electrically operated motor in the mid section for moving the movable section when the motor is operated. A second mechanism in communication with the motor for controlling the operation of the motor mechanism.

13 Claims, 20 Drawing Sheets

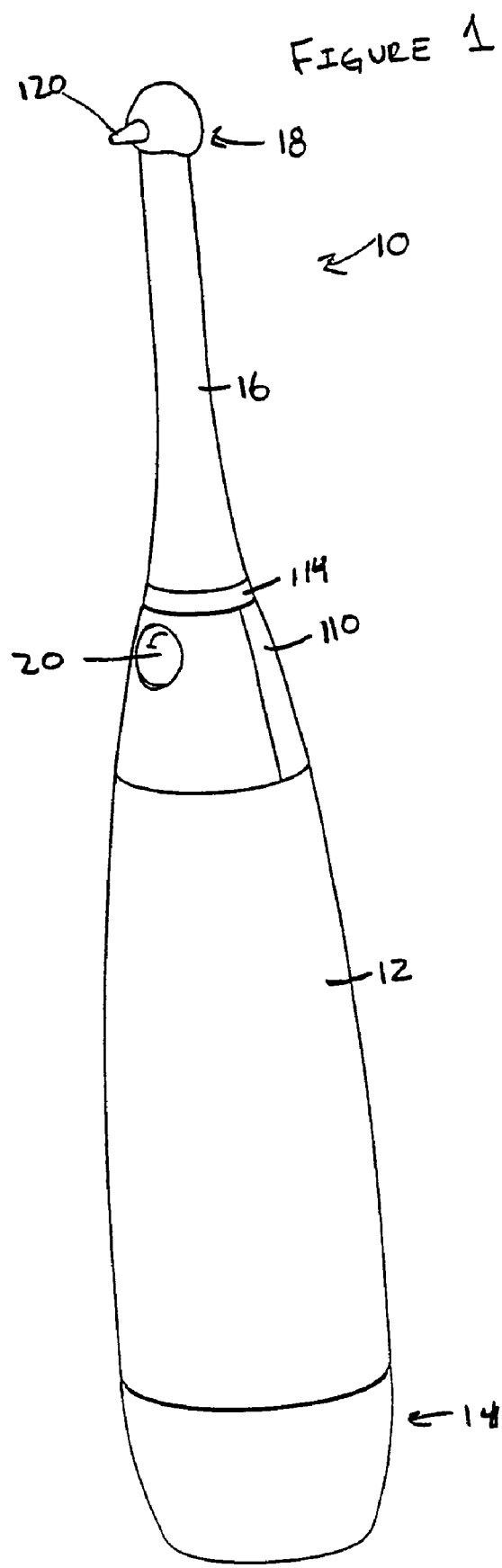

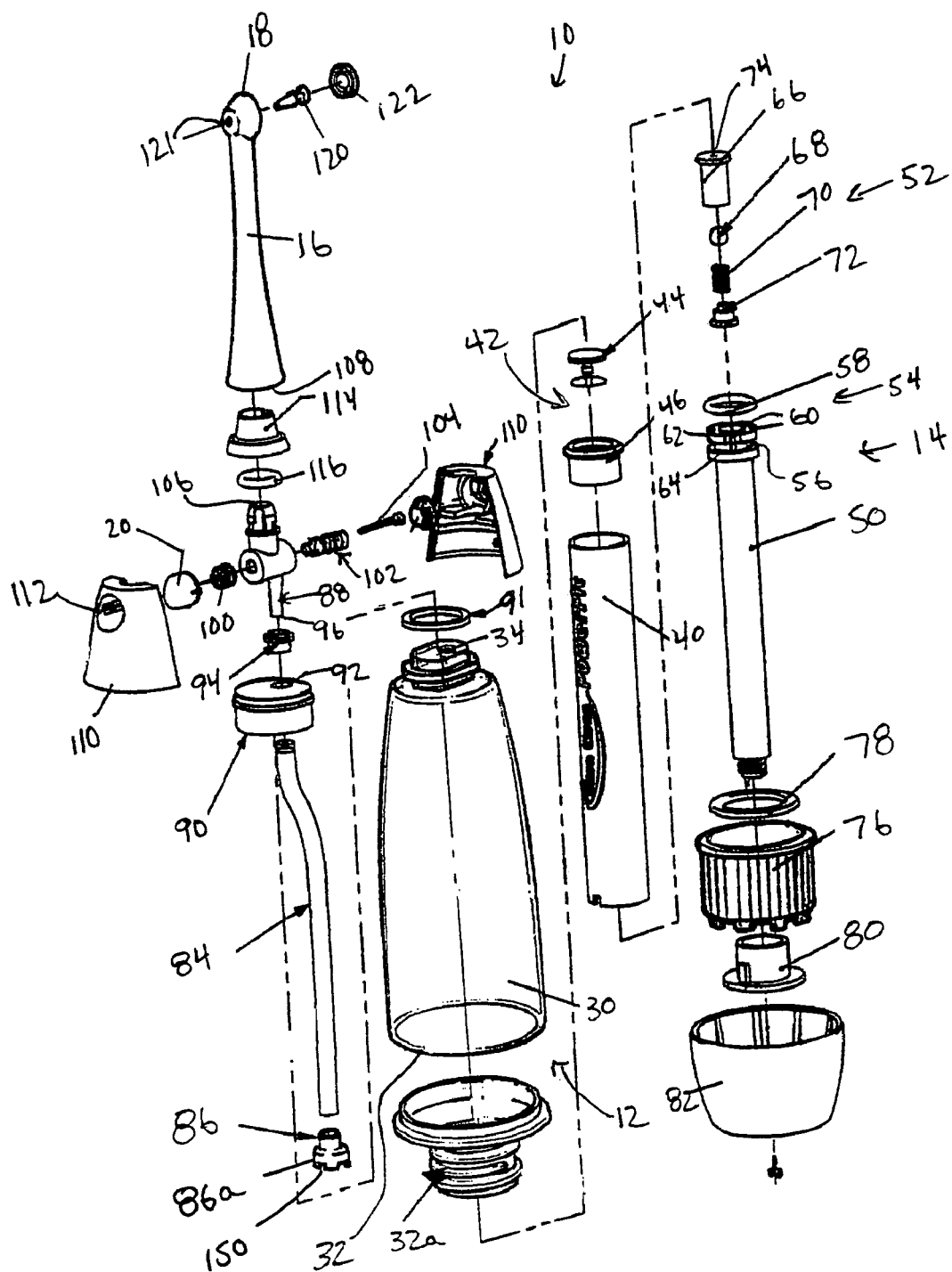

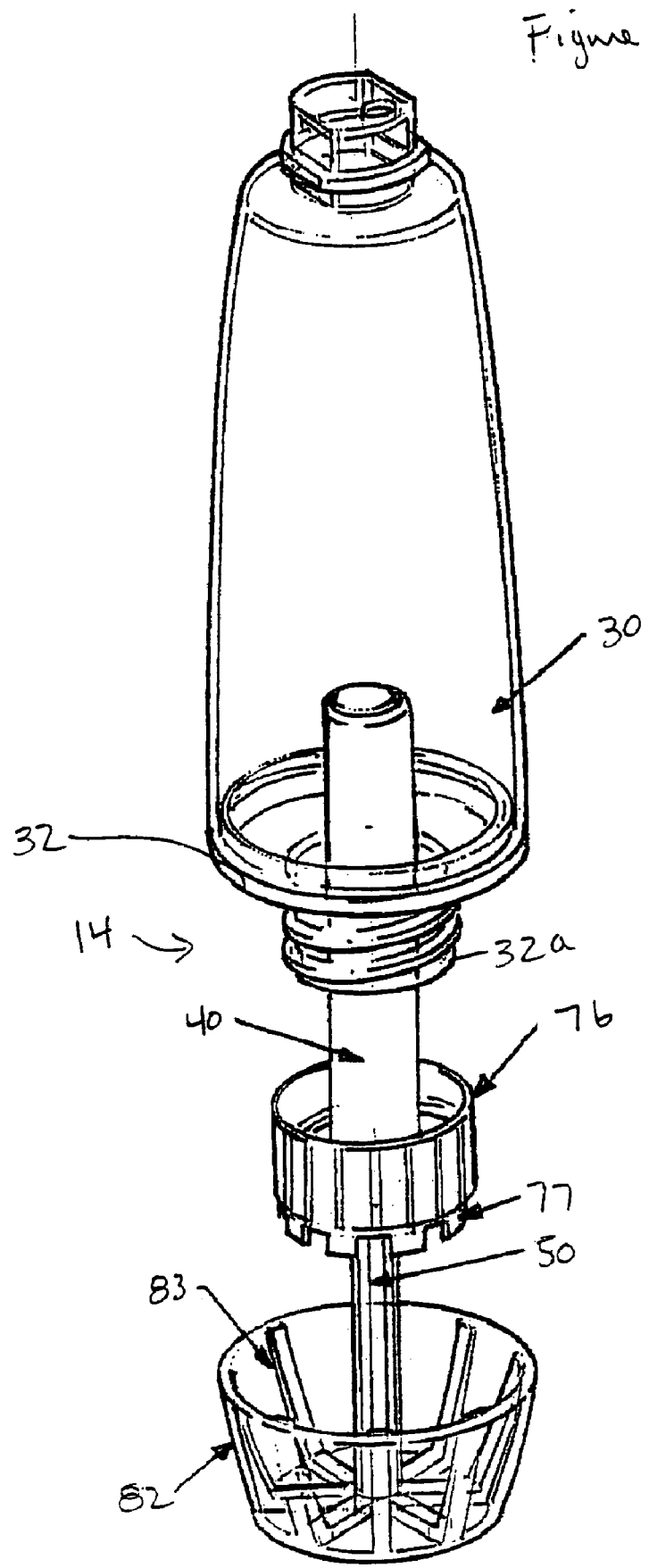

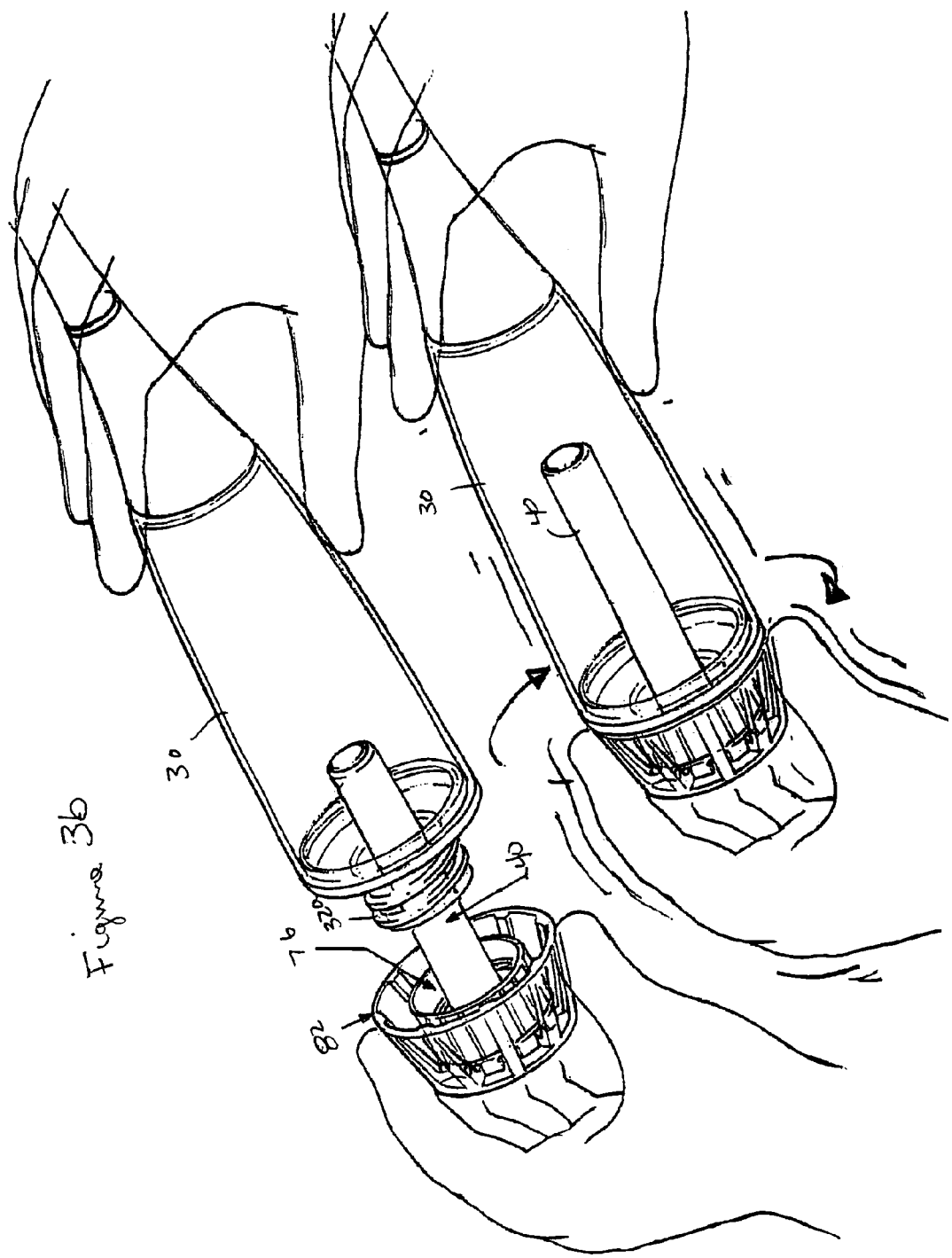

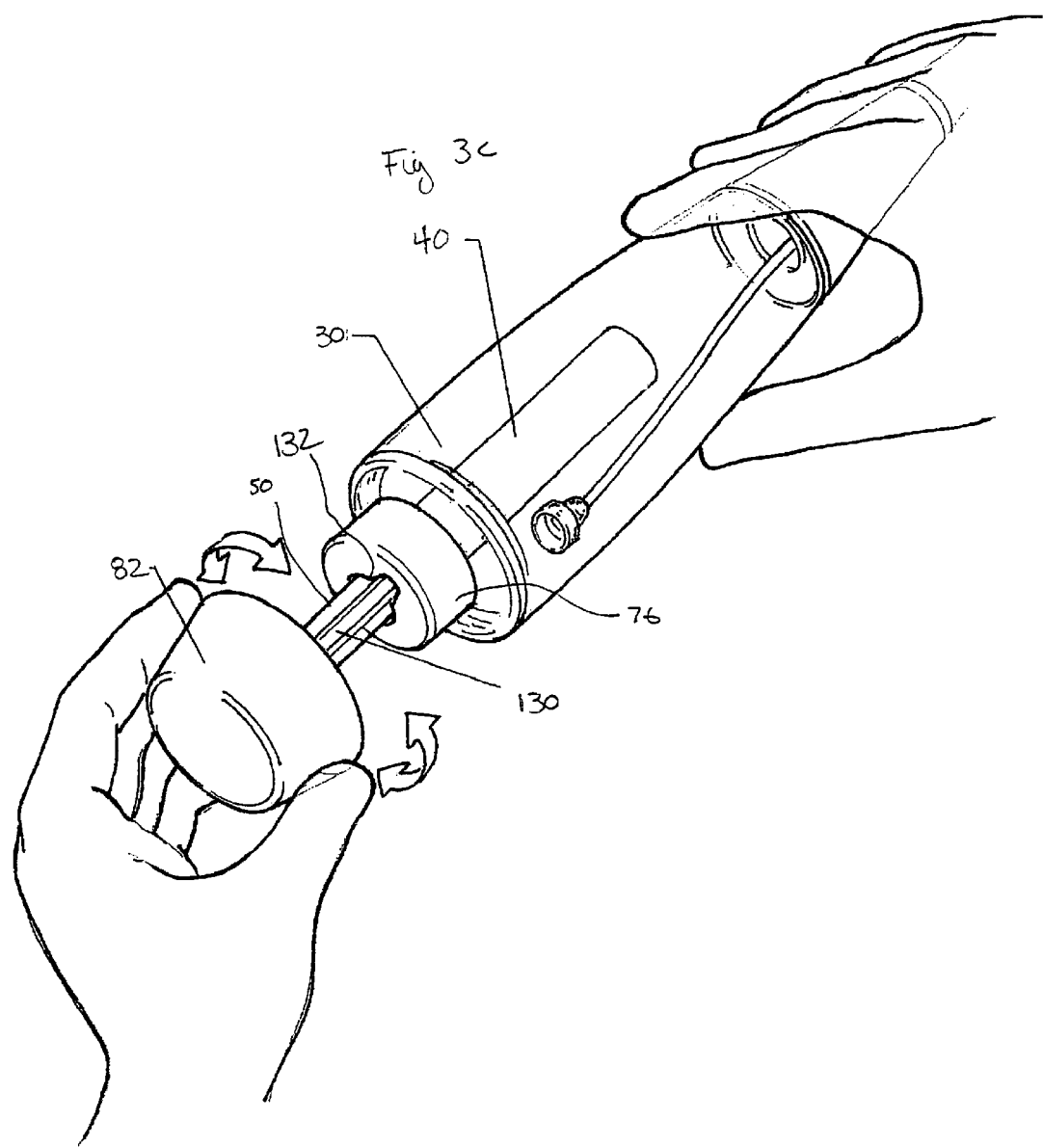

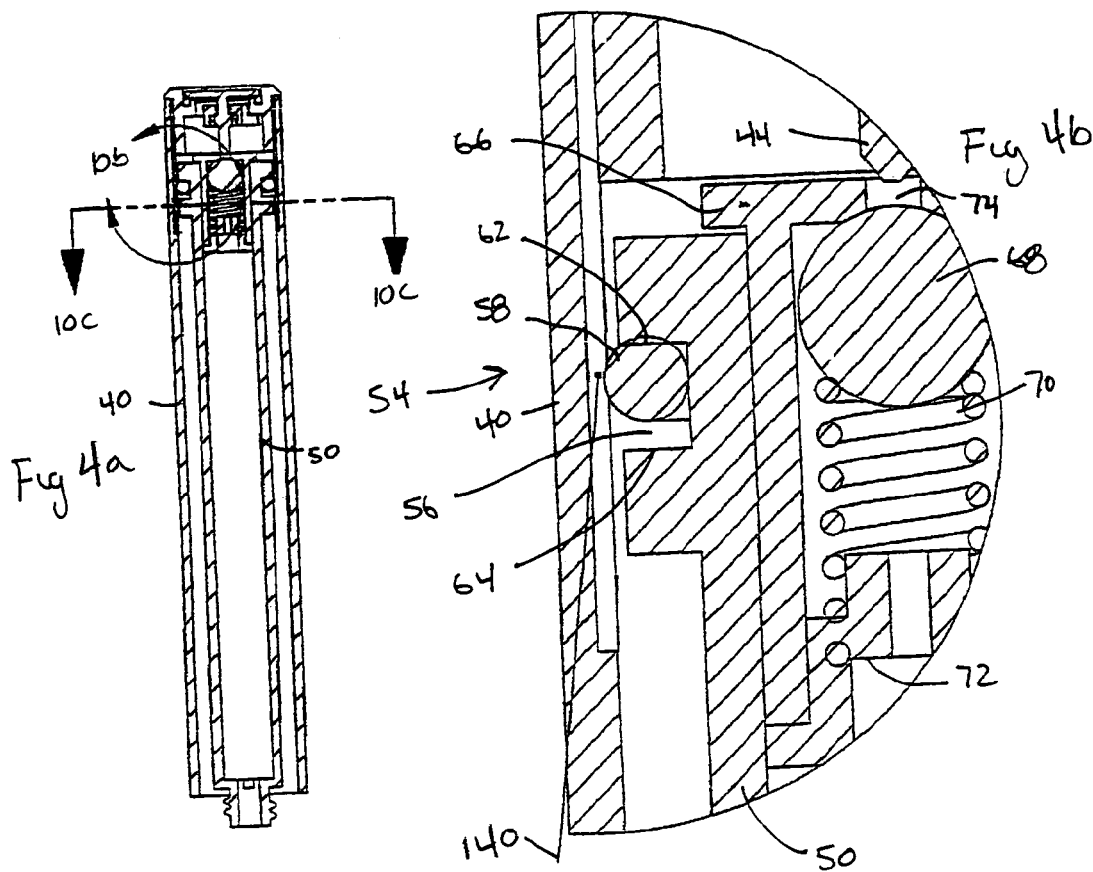
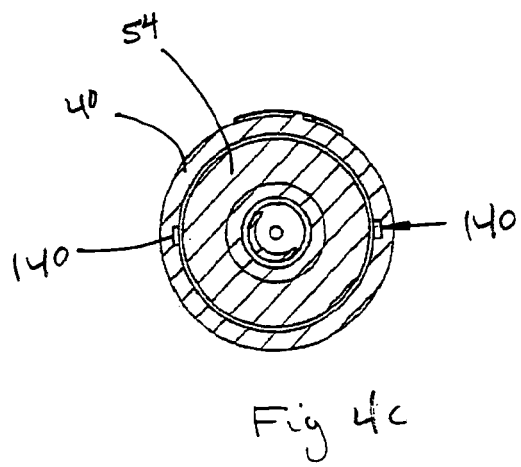

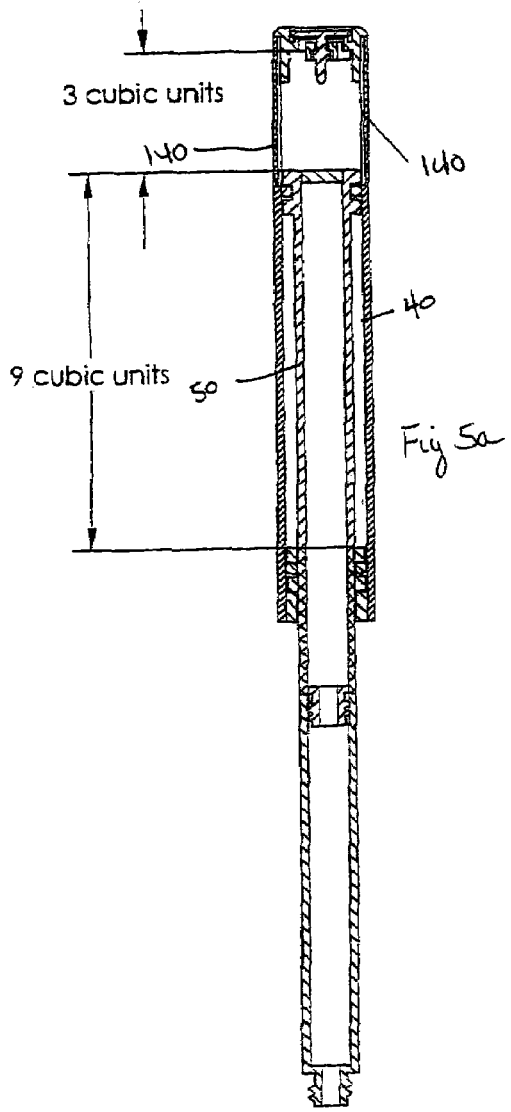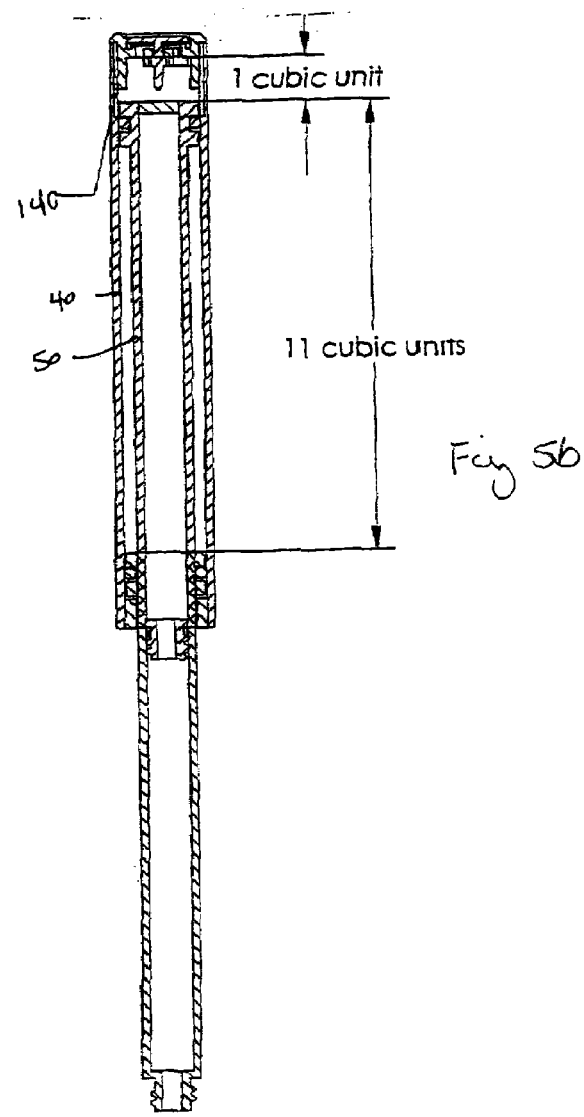

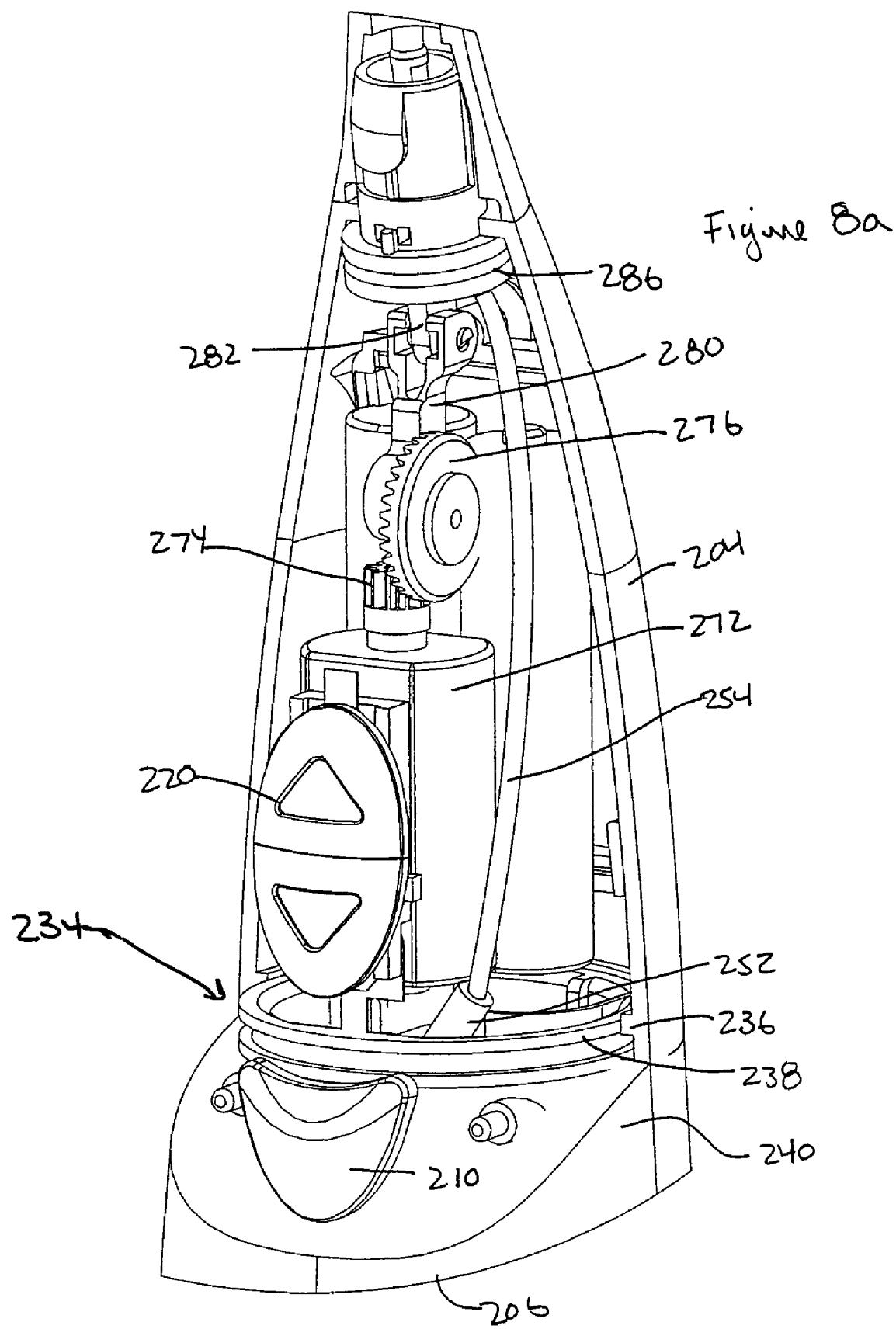

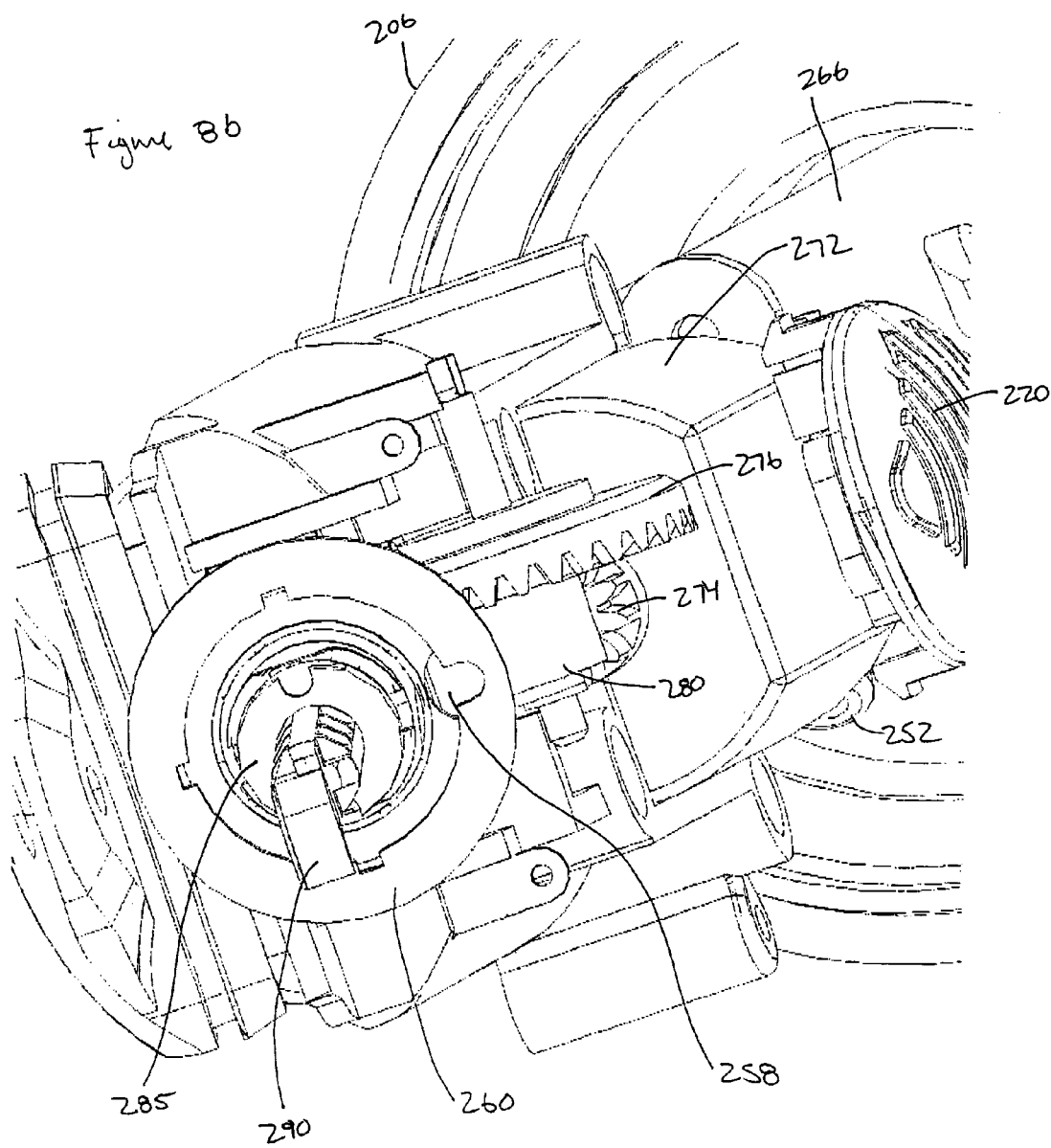

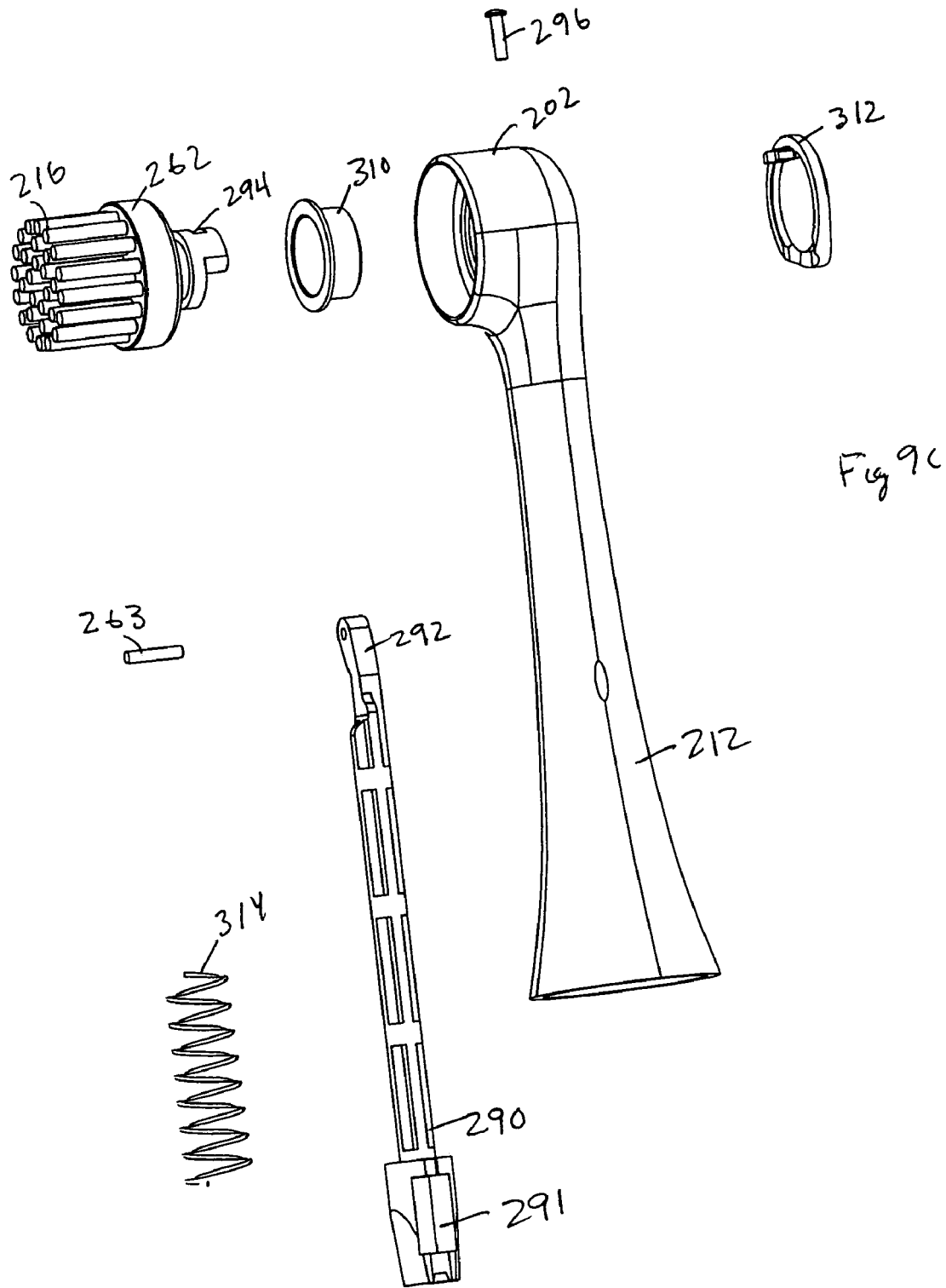

SELF-CONTAINED ORAL CLEANING DEVICE

CROSS REFERENCE TO RELATED APPLICATIONS

The present invention is a continuation in part of U.S. patent application Ser. No. 10/772,060 filed Feb. 3, 2004, now abandoned, which is a continuation in part of application Ser. No. 10/315,730 filed Dec. 10, 2002 now U.S. Pat. No. 6,689,078 which is a continuation in part of application Ser. No. 10/233,687 filed Sep. 4, 2002 now U.S. Pat. No. 6,622,333.

The present invention is also a continuation in part of U.S. patent application Ser. No. 10/987,339 filed Nov. 12, 2004, now U.S. Pat. No. 7,140,373, which is a continuation in part of U.S. patent application Ser. No. 10/886,235 filed Jul. 7, 2004, now U.S. Pat. No. 7,055,531, which claims benefit of 60/582,777 filed Jun. 25, 2004.

FIELD OF THE INVENTION

The present invention relates to oral cleaning devices such as toothbrushes and irrigators and in particular to a self-contained oral cleaning device that has a mechanically moving head and a liquid jet feature to spray liquid out of the moving head.

BACKGROUND OF THE INVENTION

Oral cleaning devices that employ an irrigator feature are known in the art and such devices use an external supply of water. In one category of the prior art, a toothbrush is tethered or connected to a faucet. The water pressure from the faucet is used to propel the water through the toothbrush and out the head of the toothbrush and/or used to power a motor that is used to rotate or move bristles. For example, U.S. Pat. No. 5,304,010 discloses a toothbrush that includes a hollow body, an opening by the head of the toothbrush, and a water inlet that is tethered and attached to a faucet. In another example, U.S. Pat. No. 4,181,997 discloses a toothbrush that is also tethered to a faucet. However, the toothbrush uses the water pressure to power an impeller to move bristles on the head of the toothbrush. In both patents, the water is already pressurized and flowing; the water also cannot be stagnant because the toothbrush does not include any mechanism, on its own, to propel the water out of the toothbrush. Additional toothbrushes that are tethered to a faucet or an external source of running water may be found in U.S. Pat. No. 5,863,192, which discloses a toothbrush tethered to a shower head; U.S. Pat. Nos. 5,500,973 and 4,257,433, which disclose toothbrushes tethered to faucets; and U.S. Pat. No. 4,412,823, which discloses a toothbrush tethered to an external source of water that is pumped into and through the toothbrush.

In another category of prior art, electric toothbrushes are connected to an external reservoir of water. For example, U.S. Pat. No. 6,047,429 combines a mechanical toothbrush with an irrigator feature. The motor used to move the bristles is also used to draw water from an outside source, not contained within the toothbrush. The water is drawn from the outside source, propelled through the neck of the toothbrush, and expelled out of the head of the toothbrush. Other electric toothbrushes which are tethered to a source of water include U.S. Pat. Nos. 4,958,629 and D318,918.

Various problems in both categories exist and are associated with the fact that the toothbrush must be tethered or connected to an outside source of water. In the first instance, when the toothbrush is tethered to a faucet, the user cannot use the toothbrush to spray other liquids such as antiseptic solutions. In the second instance, when the toothbrush is connected to an outside reservoir of water, the user's range of motion is limited as the end of the tether must remain in the outside reservoir at all times. In addition, when an electric toothbrush is tethered to an outside source, the user cannot control the force in which the water is propelled out of the toothbrush. The force is pre-set by the speed of the motor and can only be turned on or off. Furthermore, the units are bulky and are not made to be portable, oftentimes causing the user to own a separate toothbrush for traveling.

With the onset of mechanical and electrical toothbrushes the total cost of the oral cleaning devices have increased. To offset the overall price of the devices the heads of the toothbrushes have been made replaceable. As such, after the bristles become worn from continual use, the head may be replaced without replacing the whole unit. However, the worn heads are simply replaced with an identical head to provide the same type of cleaning. The ability to interchange heads to provide different types of cleaning, for example to interchange heads to provide an irrigator for rinsing, to provide a brush with water jet for cleaning teeth and gums, to provide a brush or scraper with water jet for cleaning the tongue, and to provide a flossing head with replaceable disposable floss with water jet to remove plaque between teeth, is not widely incorporated with prior art oral cleaning devices.

It is therefore an object of one embodiment of the present invention to provide a self-contained, total oral cleaning device that incorporates opening(s) for jetting a pressurized fluid onto a user's teeth. The oral cleaning device in accordance with the present invention includes a reservoir for holding a liquid and a pump for pressurizing the liquid contained in the reservoir. The reservoir is contained within the oral cleaning device eliminating the need to tether the device to a faucet or attach the device to an outside source of liquid. The oral cleaning device also includes a means for releasing the pressurized liquid contained within the reservoir out of the oral cleaning device. The oral cleaning device is completely portable and assists the user in cleaning their entire mouth, including the tongue, gums, and teeth, by providing interchangeable heads. The present invention also provides a mechanically moving head to provide oscillating bristles, or oscillating flossing head or oscillating irrigating head to provide a complete oral cleaning.

SUMMARY OF THE INVENTION

In accordance with one embodiment of the present invention, an oral cleaning device is provided with a refillable reservoir having an upper aperture. A manual operable pump is attached to the reservoir. The manual operation of the pump increases pressure within the reservoir such that the liquid contained in the reservoir becomes pressurized. A first mechanism is in communication with the reservoir for controlling the flow of pressurized liquid from exiting the upper aperture of the reservoir, thereby controlling the flow of pressurized liquid out of the device. A mid section is attached between a neck portion and the reservoir. A head is further attached to the neck portion and has an outlet for expelling pressurized liquid contained in the reservoir and further has a movable section rotatably connected thereto. A means of allowing pressurized liquid exiting the upper aperture to travel to the outlet in the head is provided in the mid section. An electrically operated motor is provided in the mid section with a means of interconnecting the motor and the movable section to move the movable section when the motor is operated. Lastly, a second mechanism is provided that is in communication with the motor for controlling the operation of the motor mechanism, thereby controlling the movement of the movable section.

In another embodiment, the device may include a neck portion that has an internal region designed to mate with an external region defined on the mid section, such that the neck portion and head attached thereto are removable from the device.

In another embodiment, various heads are provided to assist the user with different cleaning implements. For example, a brush head to clean teeth and/or their tongue as well as a jet of liquid that may assist in cleaning gums or freshening breath. Third, a head with a piece of floss and an opening to spray fluid over the floss, which assists the user in flossing between gums and teeth.

Numerous other advantages and features of the invention will become readily apparent from the following detailed description of the invention and the embodiments thereof, from the claims, and from the accompanying drawings.

BRIEF DESCRIPTION OF THE DRAWINGS

A fuller understanding of the foregoing may be had by reference to the accompanying drawings, wherein:

FIG. 1 is a front view of an oral cleaning device having a refillable reservoir that is capable of storing a liquid and having an on-board pump that is used to pressurize the liquid in the reservoir, wherein the pressurized liquid may jet from a nozzle in the head of the device to provide a user with a self-contained device that has a high pressure jet of liquid;

FIG. 2a is an exploded view of the cleaning device of FIG. 1;

FIG. 3a is a perspective view of the assembly of the reservoir with the on-board pump and illustrating mating sections on the reservoir cap and the pump handle to assist the user in tightening the reservoir cap onto the reservoir;

FIG. 3b is a perspective view illustrating the manner in which the on-board pump is threadably attached to the reservoir using the novel reservoir cap and pump handle mating sections;

FIG. 3c is an alternate embodiment of mating section defined as a pump mechanism that includes a keyed shaft that is fitted into a keyed reservoir cap;

FIG. 4a is a cross sectional view of a pump mechanism that includes channels in the cylinder to release back pressure;

FIG. 4b is a cross sectional view of the means to release back pressure illustrated in FIG. 4a;

FIG. 4c is a top view of the means to release back pressure illustrated in FIG. 4a;

FIG. 5a is a cross sectional view of a pump mechanism illustrating long channels incorporated to reduce the maximum pressure allowed into the reservoir and thus eliminating the need of a pressure release valve;

FIG. 5b is a cross sectional view of a pump mechanism illustrating shortened channels incorporated to effect the maximum pressure allowed into the reservoir;

FIG. 9c is an expanded view of the neck of FIG. 9a;

FIG. 12b is the flossing neck/head assembly of FIG. 12 a with the cap in an opened position and the flossing tool mounted in position.

DETAILED DESCRIPTION OF THE EMBODIMENTS

Figure 2B:
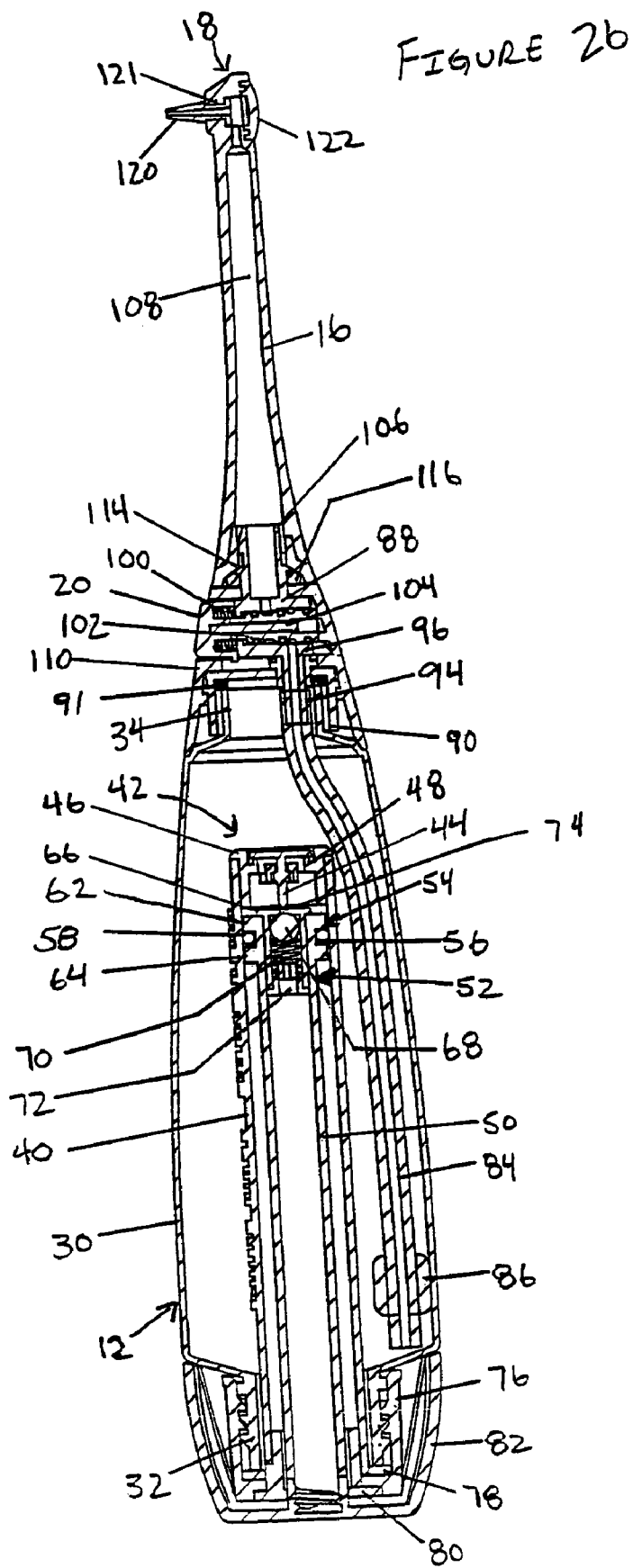
FIG. 2b is a cross-sectional view of the cleaning device of FIG. 1.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

Referring now to FIG. 1, there is disclosed an oral cleaning device generally referenced to as numeral 10. The oral cleaning device includes a body 12 (or handle) that may be gripped by a user. As will be described in detail below, the body 12 is further defined as a refillable reservoir that a user may partially fill with a fluid. The fluid may include a gas, such as air, or a liquid, such as water or an antiseptic solution used for cleaning a user's mouth and freshening breath. The oral cleaning device also includes a means for pressurizing the fluid in the reservoir. The pressurizing means is preferably an on-board pump 14. Once the fluid is pressurized, the fluid in the reservoir may be released by depressing a button 20. The button 20 opens a valve mechanism that controls the flow of the pressurized fluid out of the reservoir. The fluid once released, travels through a neck 16 that extends outwardly from the body 12 to a head 18. As illustrated in FIG. 1, the head 18 includes a nozzle 120 (which may be a soft tip nozzle) that permits a user to clean portions of their teeth and gums by jetting, spraying or releasing a liquid onto the area the user intends to clean. The neck/head assembly may be fixed onto the body 12 or preferably interchangeable with other neck/head assemblies to provide the user with different cleaning implements.

Referring now to FIGS. 2a and 2b, the oral cleaning device 10, from FIG. 1, includes a refillable reservoir 30 that also serves as a main portion of the body 12 or handle which the user grips when using the oral cleaning device 10. The refillable reservoir 30 is attached at one end (bottom aperture 32) to a reservoir threaded end 32a. The threaded end 32a may be secured to the reservoir 30 by sonic welding, or other types of securing means to provide an air tight seal about the two pieces. Alternatively, the threaded end 32a and the reservoir 30 may be blow molded as a single piece.

The reservoir 30 is attached to a removable on-board pump 14 and attached at the other end (top aperture 34) about the neck 16. Preferably, the on-board pump 14 is attached about the bottom aperture 32 such that the on-board pump 14 may be easily removed and reattached. This permits the user to pour a liquid (or other fluid) into the reservoir 30 via an opening in the threaded end 32a. However, it is also easy to implement alternative means to fill the reservoir such as but not limited to having a separate resealable inlet. In this instance, the on-board pump 14 would not have to be removable and could be permanently attached thereto.

The on-board pump 14 includes a pump cylinder 40 that slides into the reservoir 30 through the threaded end 32a and the bottom aperture 32. Secured to one end of the pump cylinder 40 is a one-way valve cap 42. The one-way valve cap 42 allows air to be pumped into the reservoir 30, which permits the user to pressurize the liquid (or fluid) inside the reservoir 30. The one-way valve cap 42 also prevents any liquid (or fluid) inside the reservoir 30 from entering the pump cylinder 40. The one-way valve cap 42 includes a flexible valve seal 44 and a valve cap 46. The valve cap 46 attaches to the end of the pump cylinder 40 and includes openings 48 to permit air to travel through. The flexible valve seal 44 is then attached to the valve cap 46 such that the flexible valve seal 44 covers the openings 48 in the valve cap 46. When the user is pumping air through the pump cylinder 40, to pressurize the reservoir 30, air in the valve cap 46 travels through the openings 48 pushing and bending the flexible valve seal 44 away from the openings 48, allowing air to enter into the reservoir 30. This also occurs when the pressure inside the reservoir 30 is lower than a maximum pressure pre-defined by a pressure release valve 52 (discussed in greater detail below). As soon as the user stops pumping air through the pump cylinder 40, the pressure in the reservoir 30 pushes against the flexible valve seal 44 and seals the openings 48, preventing liquid in the reservoir 30 from escaping via the one-way valve cap 42.

Inserted into the pump cylinder 40 is a piston shaft 50 that includes the pressure release valve 52. The piston 54 attached to the top of the piston shaft 50 has a groove 56, which receives a seal 58. The piston 54 also has notches 60 running perpendicular to the groove 56. While the piston shaft 50 is being pulled away from the pump cylinder 40, the seal 58 moves against the top portion 62 of the groove 56, allowing air to enter the pump cylinder 40, above the piston 54 via the notches 60. Subsequently, when pushed into the pump cylinder 40, the seal 58 moves against the bottom portion 64 of the groove 56, preventing air from escaping the pump cylinder 40. As such, when the piston shaft 50 is pushed into the pump cylinder 40, air inside the pump cylinder 40, above the piston 54 will be forced into the reservoir 30, again as long as the pressure inside the reservoir 30 is lower than the maximum pressure provided for on the pressure release valve 52.

When the pressure inside the reservoir 30 is greater than the maximum pressure provided for by the pressure release valve 52, the air inside the pump cylinder 40 above the piston 54 will vent through the pressure release valve 52. The pressure release valve 52 includes a release housing 66, a release ball 68, a release spring 70, and a release cap 72. The release ball 68 is held by the release spring 70 against a release aperture 74 defined in the release housing 66. When the pressure in the reservoir 30 is greater than the pressure exerted by the release spring 70 on the release ball 68, the air will push against the release ball 68 compressing the release spring 70 permitting the air to vent through the release aperture 74 and into the piston shaft 50. Eventually the air will seep out of the device 10 through pump reservoir cap 76.

The reservoir 30, pump cylinder 40, and piston shaft 50 are secured and captured by various end caps that secure them separately to the device 10. The reservoir 30 is threadably attached to a reservoir cap 76, which may be removed when filling the reservoir 30 with a liquid. A reservoir gasket 78 may be positioned between the reservoir 30 and reservoir cap 76 to prevent liquid (or fluid) inside the reservoir 30 from leaking. The pump cylinder 40 extends through the reservoir gasket 78 and reservoir cap 76 and is secured to a pump cylinder cap 80. Extending through the pump cylinder cap 80 is the piston shaft 50, which is attached to a pump handle 82. The user is also prevented from pulling the pump piston 50 entirely out of the pump cylinder 40 because the piston 54 on the piston shaft 50 is larger than an opening defined in the pump cylinder cap 80.

As illustrated in FIGS. 3a and 3b, the on-board pump 14 is shown partially expanded. The on-board pump 14 is inserted through the threaded end 32a and the bottom aperture 32. The reservoir cap 76 is then threaded or secured onto the threaded end 32a. To assist the user in threading the reservoir cap 76 onto the bottle crown 32a, the reservoir cap 76 is provided with a plurality of tabs 77 that align with raised fins 83 on the interior portion of the pump handle 82. The user places the reservoir cap 76 into the pump handle 82 such that the raised fins 83 key into spaces between the tabs 77 on the reservoir cap 76. This provides the user with an abundant amount of leverage when loosening or tightening the reservoir cap 76 onto the reservoir 30, making the process of loosening or securing the reservoir cap 76 easier.

Referring now to FIG. 3c, in an alternative configuration, the piston shaft 50 includes keyed projections 130 that are matched with grooves 132 on the bottom portion of the reservoir cap 76. When the pump handle 82 is turned, the piston shaft 50 rotates therewith, because it is secured to the inside portion of the pump handle 82. Therefore, the turning of the pump handle 82 will cause the reservoir cap 76 to be loosened or tightened.

Since the operation of the on-board pump 14 has already been partially explained, it can be further stated that when in operation a user can remove the on-board pump 14 by separating the reservoir cap 76 from the reservoir 30. This permits the user to partially fill the reservoir 30 with a liquid or other fluid. The reservoir 30 is preferably made of a clear material to allow the user to view the amount of liquid in the reservoir 30. However, the reservoir may be partially covered leaving a section or window area uncovered such that the user may view the inside portion of the reservoir 30. Alternatively, since the filing of the reservoir 30 is from the bottom aperture 32, the user may view the filing process therethrough eliminating the need to view through any portion of the reservoir. After partially filling the reservoir 30, the user re-attaches the on-board pump 14 by inserting the pump cylinder 40 into the reservoir 30 and securing the cap 76 to the reservoir 30. The user then can extend the piston shaft 50 out of the pump cylinder 40 by holding both the pump handle 82 and the reservoir 30 and pulling the pump handle 82 away from the reservoir 30. Air will then enter the pump cylinder 40 by the piston 54. The user then pushes the piston shaft 50 back into the pump cylinder 40, forcing air through the one-way valve cap 42 and into the reservoir 30. Repeatedly pumping air into the reservoir 30 will pressurize the liquid contained therein. Since excess pressure is not desired, when the pressure inside the reservoir 30 is substantially equal to the maximum pressure set by the pressure release valve 52, the air will no longer enter the reservoir 30 but will instead vent out of the pump cylinder 40 through the pressure release valve 52. Once the fluid or liquid inside the reservoir 30 is pressurized the user may release the pressurized liquid through a nozzle located in the head 18 of the oral cleaning device 10.

It may be further stated that the user can alter not only the force of the jetting liquid (or fluid) exiting the device 10 but also the duration such force is maintained. To alter the force of the jetting liquid (or fluid), the user may learn that for a specific water level inside the reservoir the user must pump air into the reservoir ten times (pressurizing the reservoir to a desired pressure). By reducing the number of times the user pumps air into the reservoir, the desired force of the liquid (or fluid) jetting out of the device 10 will decrease. In addition, the duration the force of the liquid (or fluid) jetting out of the device 10 is directly related to the level of liquid (or fluid) inside the reservoir for a specific pressure. As such, if the user reduces the liquid or (or fluid) level, but maintains the desired pressure inside the reservoir 30, the duration this desired force is maintained will increase. Similarly, if the user increases the liquid (or fluid) level, the duration of force or pressure will decrease. As such it may be preferred to have a fill line on the reservoir 30 that permits the user to fill the reservoir to a predetermined amount. This would provide the user with an optimum force of jetting liquid (or fluid) (when pressurized to the maximum pressure) for an optimum maximum duration. In addition, the secondary fill lines can relate to various head attachments, providing optimum settings for different cleaning tasks.

The invention may also utilizes a means to release any back pressure that has built up during the pumping process. Illustrated in FIGS. 4a through 4c, the piston cylinder 40 may include channels 140 about the top portion of the cylinder 40. When the piston 54 reaches the top portion of the cylinder 40 the back pressure is released around the seal 58 positioned in the groove 56 of the piston 54 via the channels 140. This also keeps prevents the piston shaft 50 from being pushed outwardly at a high pressure, when the user stops pumping.

Moreover, it has be found that the length of the channels 140 effects the amount of maximum pressure allowed to be pumped into the reservoir 30. If the maximum pressure allowed into the reservoir 30 is dropped below the maximum pressure the reservoir 30 can hold without popping, then the pressure release valve 52 may be eliminated. Referring now to FIGS. 5a and 5b, given a set length defined by the cylinder 40, the longer the channels 140 the lower the maximum pressure allowed into the reservoir 30. Illustrated in FIG. 5a, the cylinder 40 is 12 cubic units with channels 140 that are 3 cubic units, leaving only 9 cubic units for which the piston can travel before the back pressure is released. The maximum pressure (psi) possible, using standard pressure formula, that could enter the reservoir would thus be the total cubic length (12) divided by the length of the channel (3) times the conversion of atmospheric pressure to psi (14.7) or 58.8 maximum psi possible. Illustrated in FIG. 5b, the cylinder 40 is still 12 cubic units but the channels 140 are shortened to 1 cubic unit, leaving all 12 cubic units for which the piston can travel. Using the same pressure formula, the maximum pressure possible into the reservoir is (12) times (14.7) or 176.4 psi. If the reservoir 30 is only rated to handle a maximum pressure of 100 psi, then either a pressure release valve must be installed or the channels 140 must be a length that would reduce the pumping force such that the maximum possible pressure inside the reservoir is rated pressure or 100 psi.

Referring back to FIGS. 2a and 2b, to transport the liquid (or fluid) from the reservoir 30 to the nozzle, a hose or tube 84 is placed through the top aperture 34 of the reservoir 30 and into the reservoir 30. The length of the hose may vary and the flexibility of the hose may vary depending upon use. The tube or hose 84 may contain a cap 86 on the end of the hose that is placed within the reservoir 30 and includes an annular opening (not shown) such that pressurized liquid may travel through the cap 86 and into the hose 84. The cap 86 may also be weighted to keep the opened end of the hose 84 near the bottom of the reservoir 30, which in turn helps evacuate the entire contents of the reservoir 30, even if the user is tilting or turning the device 10. However, when jetting the contents out of the reservoir 30 through the hose 84, a vacuum effect is created in the hose 84, by the release of pressure in the reservoir 30 therethrough, such that it is possible that the hose 84, if flexible or long enough, stretches itself to a length that the end of the hose 84 attaches or vacuum seals itself against an interior wall of the reservoir 30, thereby preventing fluid from escaping. To prevent this from occurring, a cap 86a, illustrated in FIG. 2a, can include a plurality recessed or grooved channels 150 that lead into a centered aperture to prevent the entire end from becoming vacuum sealed against the wall of the reservoir 30 during evacuation of the reservoir 30.

Referring back to FIGS. 2a and 2b, the other end of the hose 84 is attached to a releasing/preventing mechanism 88 that when activated allows the pressurized liquid or fluid to travel through the neck 16 and out of the device 10. The other end hose 84 is preferably secured through an opening 92 in a top reservoir cap 90 that is secured to the top aperture 34 of the reservoir 30, along with a top reservoir gasket 91. The opening 92 is reinforced with a grommet 94 that places the hose 84 in fluid communication with an inlet 96 defined in the releasing/preventing mechanism 88. The releasing/preventing mechanism 88 also includes a valve piston 102 that may be moved to an open position (allowing pressurized liquid or fluid to travel through) by a button 20. A valve spring 100 exerts a force onto the button 20 and the valve piston 102 that normally keeps the releasing/preventing mechanism 88 in a closed position (not allowing pressurized liquid or fluid to travel through). A valve pin 104 holds the button 20 in position with the valve piston 102 and valve spring 100. The releasing/preventing mechanism 88 and other components described for opening and closing the mechanism 88 is housed within a two piece housing 110. The front portion of the housing 110 includes an opening 112 to permit the button 20 to be pressed by a user. As mentioned, the releasing/preventing mechanism 88 is in a closed position unless the button 20 is pressed and held down by a user.

When activated, the pressurized liquid or fluid travels through the releasing/preventing mechanism 88 and out an exit 106 defined thereon. The exit 106 of the releasing/preventing mechanism 88 is in fluid communication with a channel 108 running through the neck 16. The neck 16 is secured to a neck base 114 that is removably attached to the exit 106. A neck o-ring 116 is preferably positioned between the neck base 114 and the two piece housing 110. The channel 108 travels through the neck 16 to at least one opening 121 in the head 18. Preferably a nozzle is positioned in the opening 121, in communication with the channel 108, and held in place by a nozzle cap 122.

Figure 6:
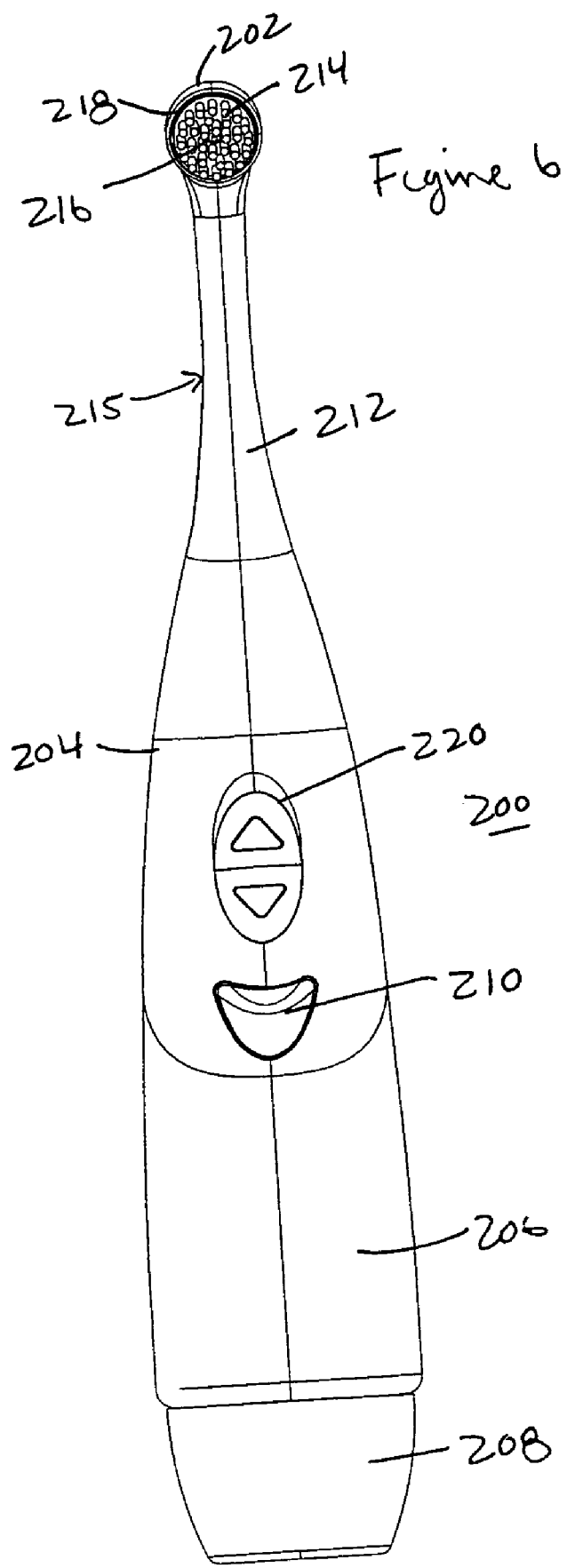
FIG. 6 is a front view of an oral cleaning device having a refillable reservoir with an on-board pump used to pressurize liquid therein, wherein the pressurized liquid jets from an opening in the head of the device; the oral cleaning device further includes a motor mechanism to move a section of the head, thus providing a self-contained oral cleaning device that has a moveable head and a stream of liquid.

In accordance with the present invention, a complete oral cleaning device 200 is illustrated in FIG. 6. The device 200 not only includes a means to spray a pressurized liquid out of the head 202 of the device similar to the previous embodiment, but also includes a means to move a section of the head 202 to provide moving, oscillating or vibrating bristles or flossing heads, or irrigating heads.

The device 200 includes a body 204 (or handle) that may be gripped by a user. The body 204 has a reservoir 206 defined in the lower portion thereof that a user may partially fill with a fluid. The oral cleaning device also includes a means for pressurizing the fluid in the reservoir 206. The pressurizing means is preferably an on-board pump 208. Once the fluid is pressurized, the fluid in the reservoir may be released by depressing a first button 210. The first button 210 opens a valve mechanism that controls the flow of the pressurized fluid out of the reservoir. The fluid once released, travels to and through the neck 212 that extends outwardly from the body to the head 202. The neck and head form an assembly 215 that may be removed from the device 200.

As illustrated in FIG. 6, the head 202 includes an aperture 216 (which may include a nozzle) with surrounding bristles 214. This type of brush head 202 permits the user to brush their teeth and/or gums while releasing liquid from the reservoir 206 onto the area the user intends to clean. The neck/head assembly 215 is preferably interchangeable with other neck/head assemblies to provide the user with different cleaning implements.

An additional advantage over the prior art is the present invention also includes a movable section 218 on the brush head to which the bristles 214 are secured thereto. The movable section 218 is mechanically operated to rotate or oscillate. To activate the movable section, the device 200 is equipped with on/off switches 220. It being well known in the art to simply provide a single on/off switch that when pressed activates the movable section and when released deactivates the movable section. As described in greater detail below, the device includes a power supply (either removable or rechargeable) to power a motor mechanism used to move the movable section.

Figure 7:
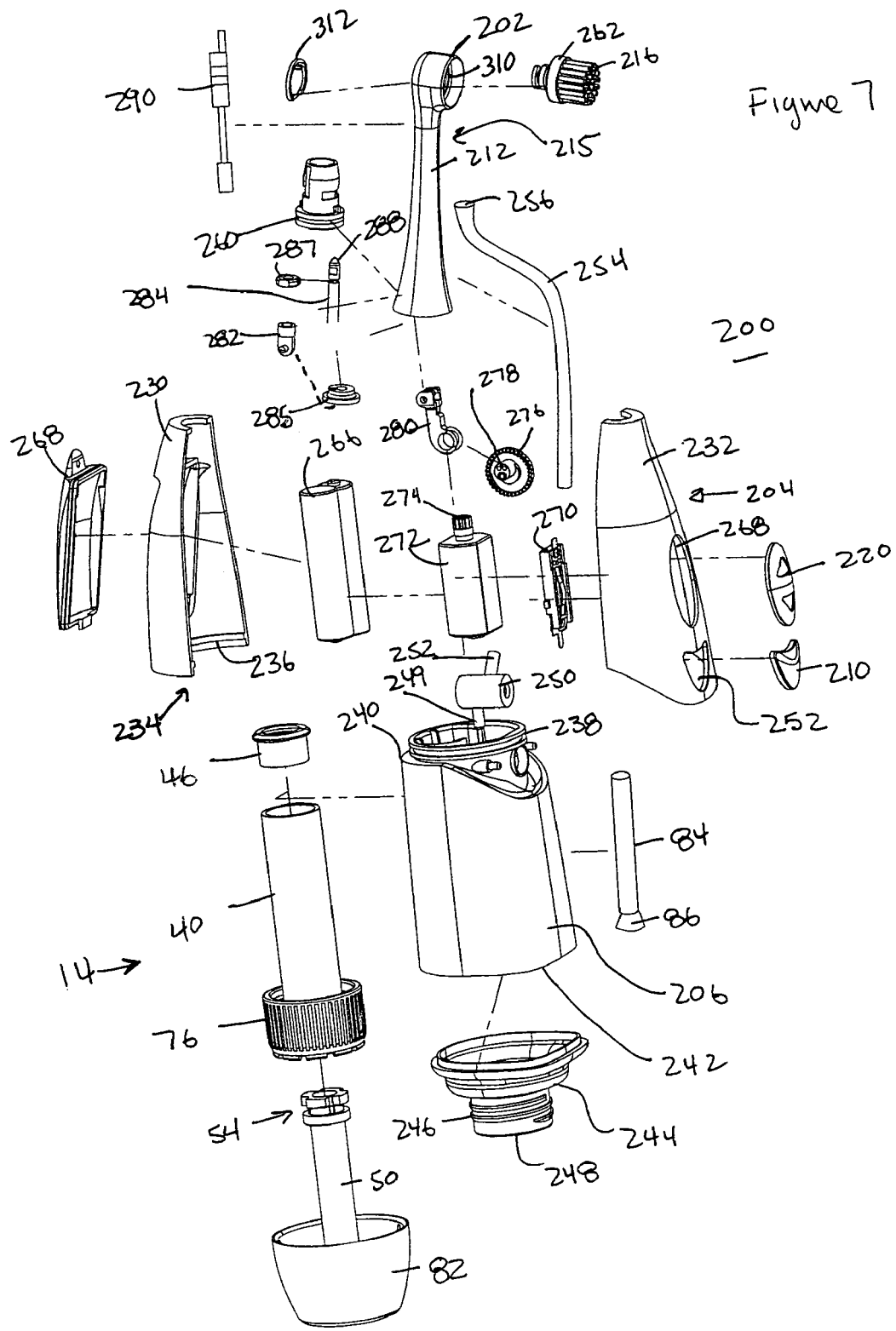
FIG. 7 is an exploded view of FIG. 6.

Referring now to FIGS. 7 through 9b, as mentioned, the oral cleaning device 200 includes a body 204, which is shown in FIG. 7 as a two piece body housing 230, 232 that is assembled to house various components used to operably move the moveable section of the head (discussed in greater detail below). Secured to one end 234 of the body 204 is the reservoir 206. To secure the body 204 to the reservoir 206, the body 204 includes an annular flange 236 that is secured into a groove 238 on a top portion 240 defined by the reservoir 206. A bottom portion 242 of the reservoir 206 includes a reservoir end 244 that is either threaded or welded to the bottom 242. The reservoir end 244 does include a bottom thread 246 that secures to the inside of the reservoir cap 76. The reservoir end 244 includes an aperture 248 to permit the reservoir to be refilled with a liquid when the reservoir cap 76 is unscrewed and the pressurizing means or on-board pump 14 is removed. The on-board pump 14 is described above and further explanation is therefore not necessary.

The tube 84 that is placed in the reservoir 206 is secured to an inlet 249 defined by a first control mechanism 250 for controlling the flow of pressurized fluid from exiting the reservoir 206. The first control mechanism 250 is manually operated by a button 210 that extends out of an opening 252 in the body 204. Similar to the valve mechanism 88 described above, the first control mechanism 250 when operated allows the pressurized fluid from the reservoir 206 to exit an outlet 252 defined thereby. The pressurized fluid travels from the outlet 252 up through a tube 254 or channel in the body 204 to the neck 212. The end 256 of the tube 254 is secured to a neck inlet 259 defined in the neck base 260 (FIGS. 8b and 8c), the neck inlet 259 includes an opening 258. The neck base 260, as described below in greater detail, permits the neck 212 and head 202 (defined together as a neck/head assembly 215) to be removed from the body 204 and replaced or interchanged with other neck/head assemblies. The neck 212 is bored throughout the interior thereof such that the pressurized fluid travels through the opening 258 in the neck base 260 into the interior of the neck 212. The pressurized fluid will travel through the neck 212 to the head 202 and exit through a nozzle, an aperture, or an opening 216.

The oral cleaning device 200 also includes a means to move, oscillate or rotate a portion or section 218 of the head 202. The means to move the movable section 218 is defined by including a motor 272 that is energized by a power supply 266 (such as a replaceable battery pack or may be energized by a rechargeable battery pack). A battery door 268 may be included when the power supply 266 is replaceable. Activation of the motor 272 is manually controlled through an on/off switch 220 that is manipulated externally from the device. The switch 220 extends through an opening 268 in the body 204. The switch 220 is connected to electrical contacts on a switch board 270 that is connected to the power supply 266 and a motor 272. The motor 272 drives a transmission assembly that connects to the movable section 262, such that when the motor 272 is activated the movable section 262 moves.

The transmission assembly may be described as having a drive gear 274 meshed to a crown gear 276. Secured to the crown gear is a cam 278 that is attached to a cam rod 280. As the drive gear 274 rotates, the cam 278 moves around the crown gear causing the cam rod 280 to move laterally up and down. Thereby the transmission assembly converts the rotational movement of the drive gear 274 into a lateral movement of the cam rod 280. Attached to the end of the cam rod 280 is a follower 282 that is secured to a link 284 through a pneumatic boot seal 285. The boot seal 285 is flexible such that as the follower 282 moves upwardly the boot seal 285 stretches upwardly and when the follower 282 moves downwardly, the boot seal 285 compresses. The boot seal 285 includes a lower gasket 300 to assist in preventing liquid from traveling downwardly from the neck 212 into the motor compartment or body 204 of the device 200. As mentioned above the pressurized fluid will travel through the neck inlet 259 and enter the interior of the neck base 260 via an aperture 302 above a boot seal 285.

Figure 8G:
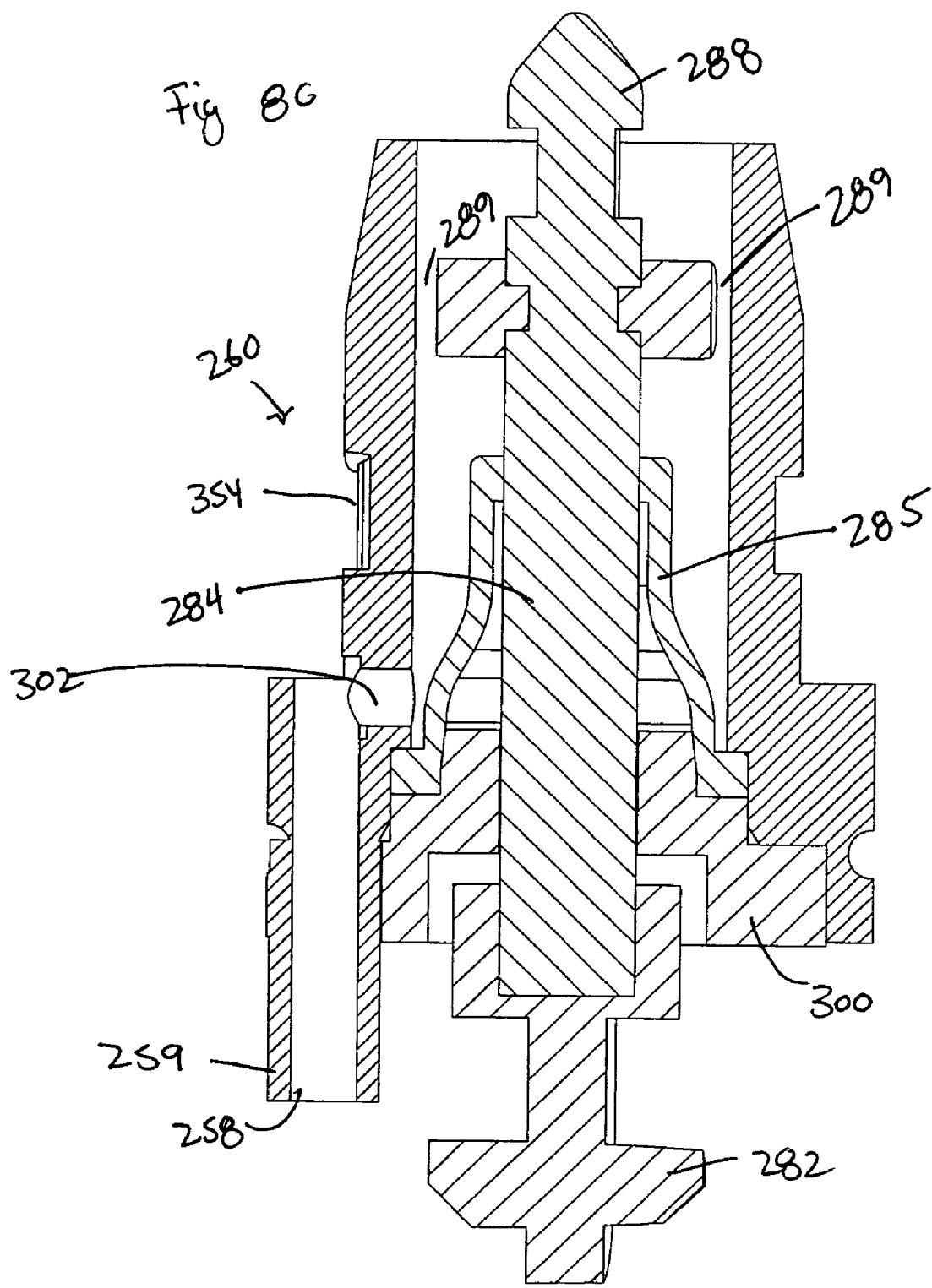
FIG. 8a is a detailed view of the motor mechanism and transmission assembly included in the device of FIG. 6.
FIG. 8b is a top expanded perspective view of a neck base used to secure a neck/head assembly to the device of FIG. 6.
FIG. 8c is a cross sectional view of the neck base.
Figure 9A:
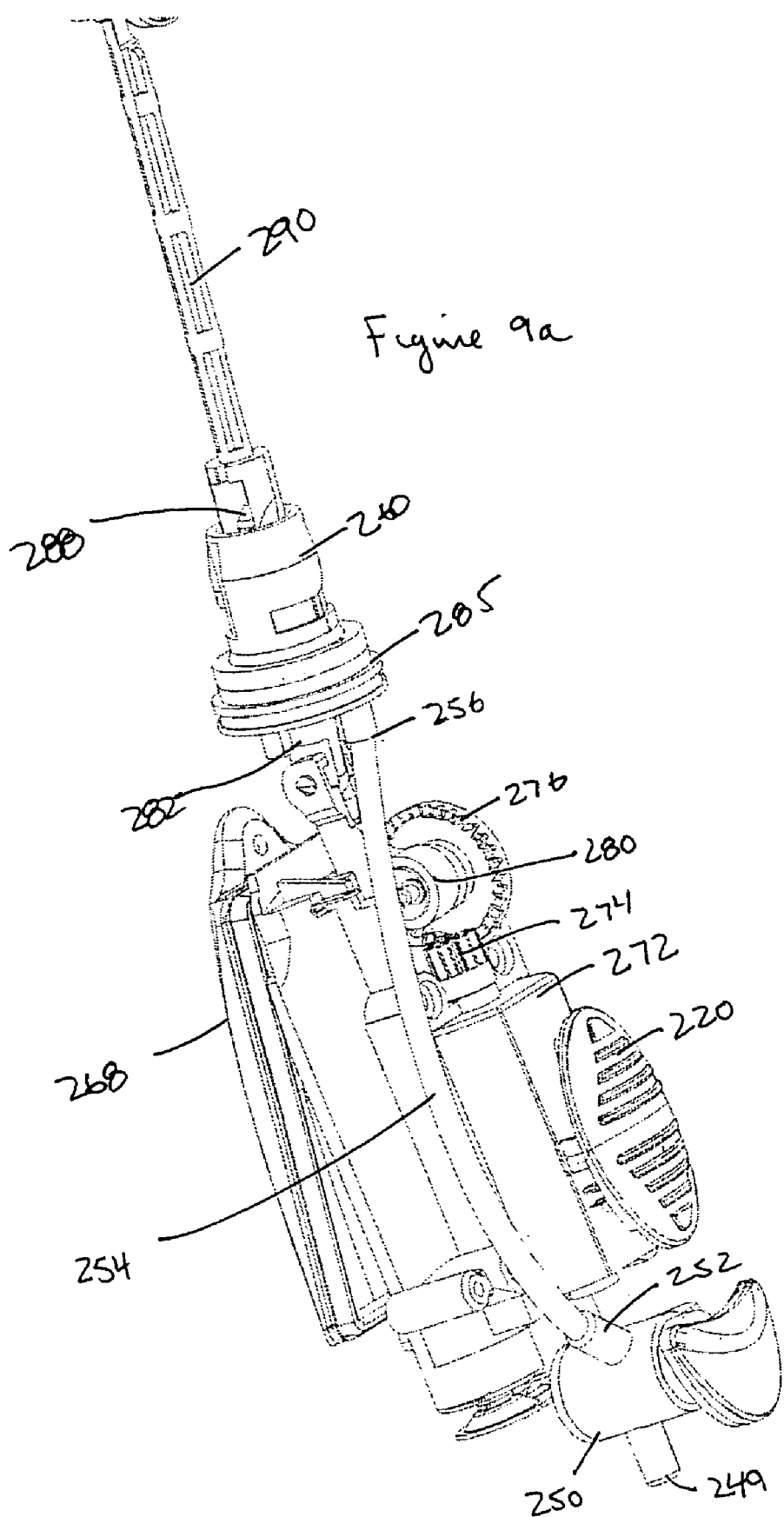
FIG. 9a is a view of internal components from the valve mechanism to the head of the device of FIG. 6 to illustrate the motor mechanism and transmission assembly.

Referring now to FIGS. 8c and 9c, the link 284 extends through the neck base 260. A neck rod 290 includes a clip portion 291 on its end that secures to a barb 288 or end of the link 284 extending the lateral up and down movement of the link 284 through the neck/head assembly 215. To help controller the lateral movement of the follower 282, a guide 287 is attached along the length of the follower. The guide includes notches 289 so the flow of liquid is not impeded.

Figure 9B:
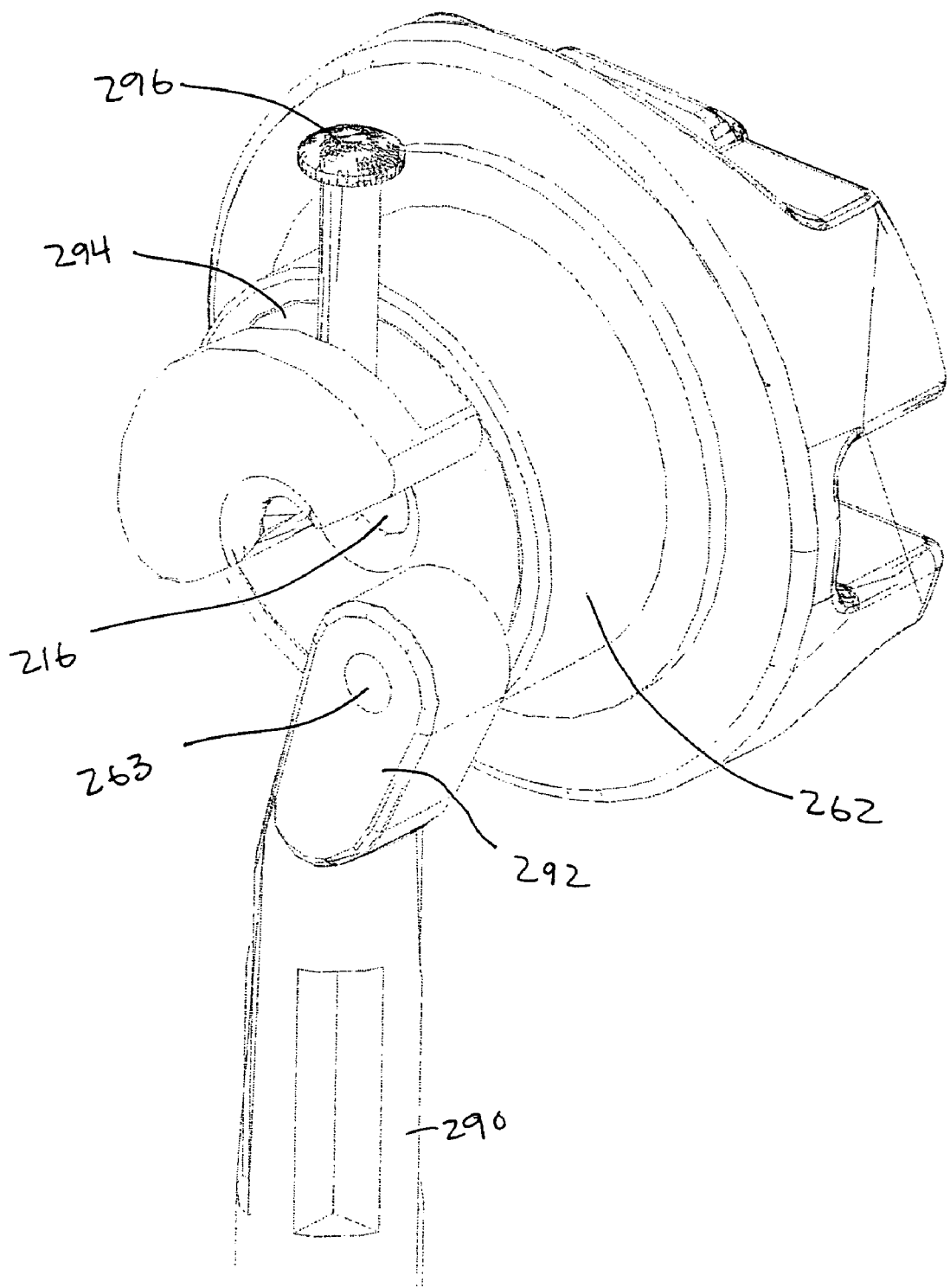
FIG. 9b is a back view of the head of the device of FIG. 6 illustrating a neck rod used to move a section of the head.

As shown in FIGS. 9b and 9c the neck rod 290 has an upper end 292 secured to the moveable section 262 via a pin 263. As the neck rod 290 moves laterally, the moveable section oscillates back and forth. To assist in limiting the oscillation or movement, the moveable section 262 may include a notched backside 294 with a pin 296 riding therein which is also secured to the neck/head assembly 215. When the moveable section 262 moves, the pin 296 secured to the assembly 215 will contact the edge of the notched backside 294 limiting further movement in the same direction. The moveable section 262 moves within a circular guide 310 that is secured to the head 202 of the device 200. A cap 312 is secured thereto to hold the components in place. The further help with returning the neck rod 290 to the bottom position a spring 314 is provided which keeps the neck rod 290 biased downwardly. During movement, the neck rod 290 is moved upwardly and downwardly as described above, oscillating the moveable section. If the movement is stopped, the spring helps ensure the moveable section returns to its initial position, which may be in the case of the flossing head to have the flossing head in a substantially straight position.

Figure 10:
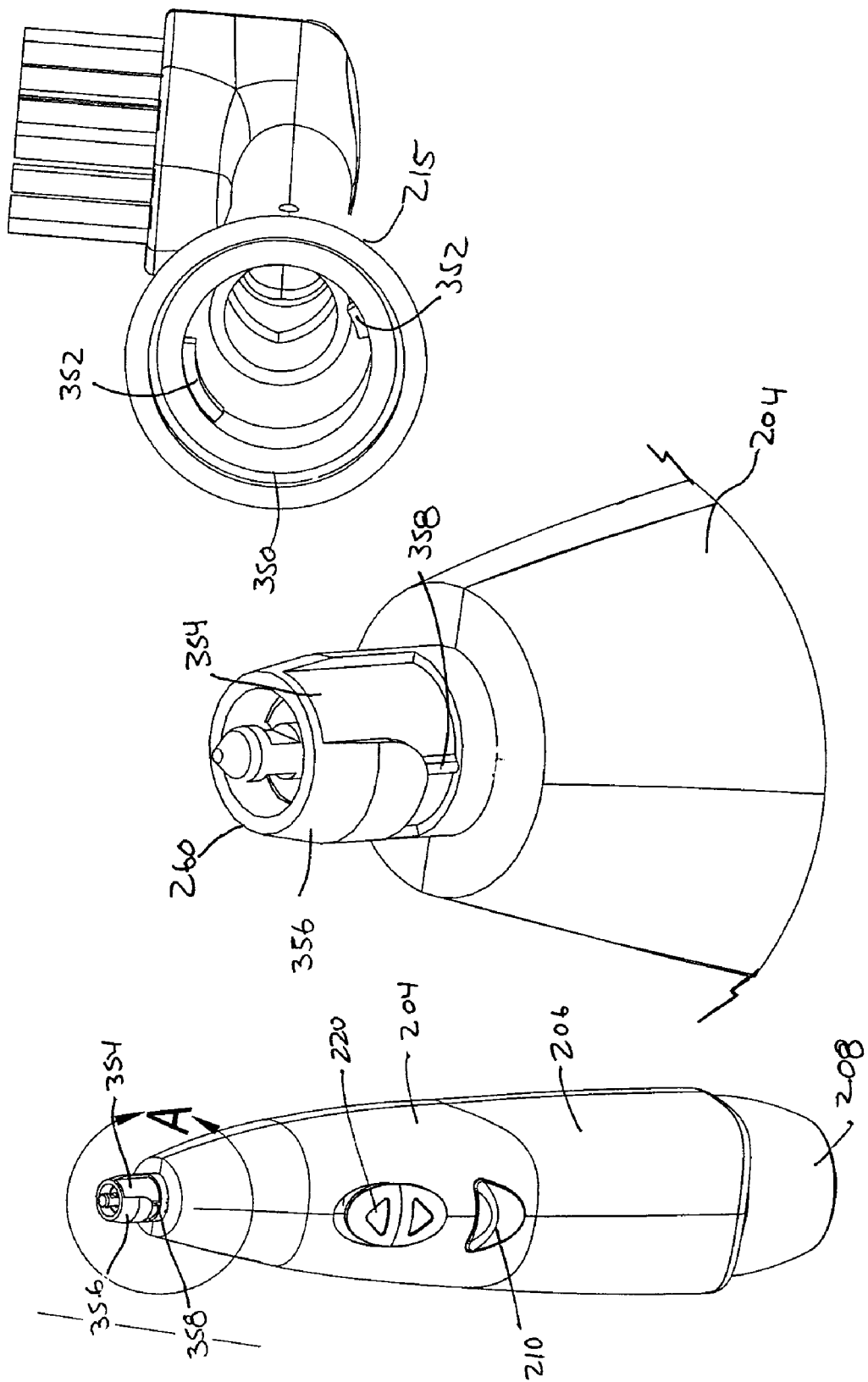
FIG. 10 is an external view of the device with an enlarged view of the neck base illustrating the connection used to removably secure the neck/head assembly to the device.

As shown in FIG. 10, the neck/head assembly 215 is preferably removable from the body 204 of the device 200 and interchangeable with other neck/head assemblies. This allows for a total oral cleaning experience. The neck/head assembly includes an internal region 350 with tabs 352 extending inwardly. The tabs 352 fit into grooves 354 on an external region 356 defined on the neck base 260. The neck/head assembly 215 is slid onto the neck base 260 and turned to until the tabs 352 slide over a detent 358 positioned in the groove 354.

Figure 11:
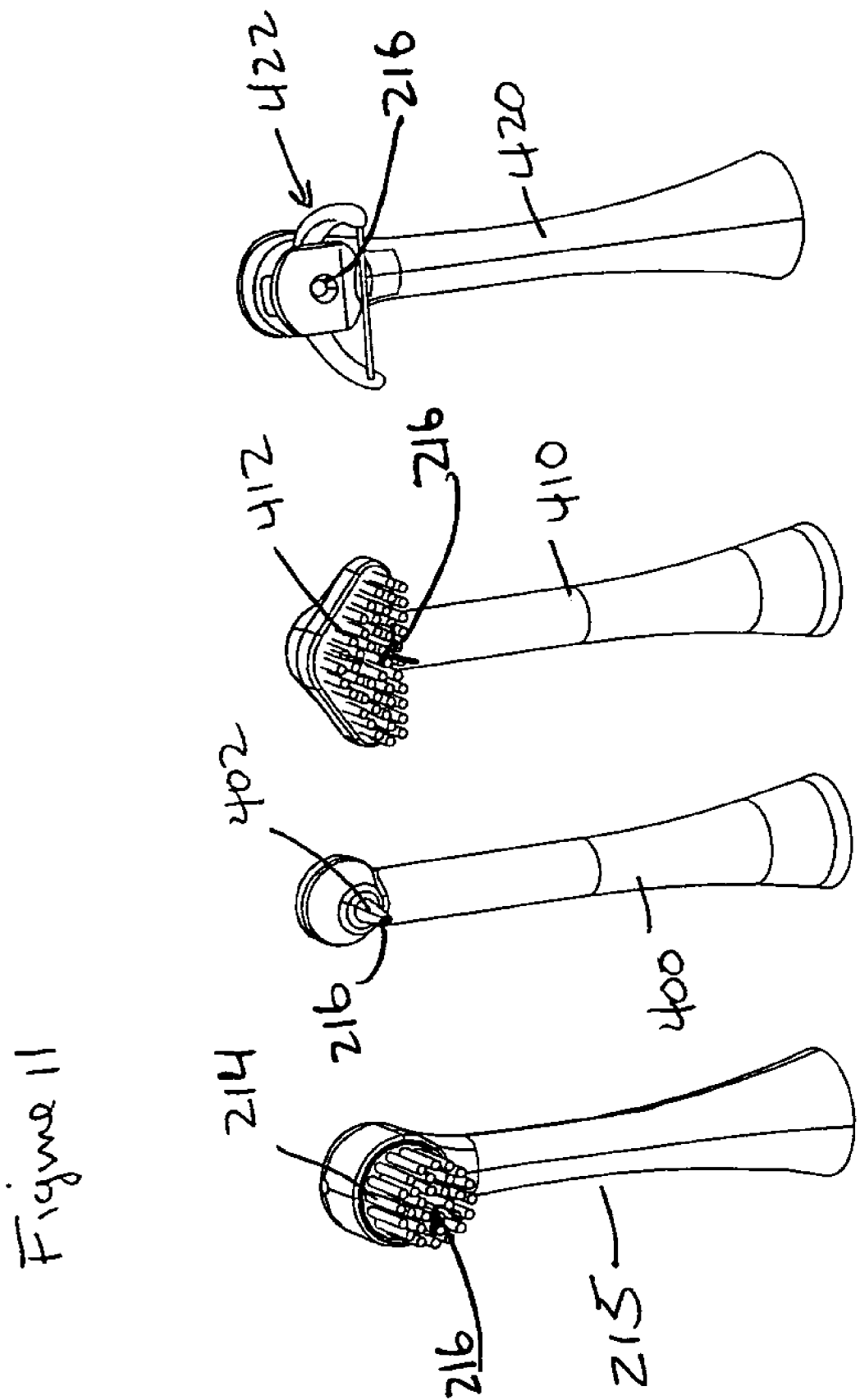
FIG. 11 depicts alternate neck/head assemblies.

Referring now to FIG. 11, the first neck/head assembly 215 as described above, includes bristles 214 that oscillate and surround an aperture 216. A second neck/head assembly 400 includes a soft tip nozzle 402 that provides a pinpoint jet of liquid into the users mouth. The user can place the soft tip nozzle 402 in between the teeth and gums to simulate a water pick action. It being shown that the present device 200 may be used with neck/head assemblies that do not include movable sections. A third neck/head assembly 410 includes a plurality of bristles 412 but contains a wider cross section than the first neck/head assembly. This provides the user with a cleaning device that is better suited to clean the user's tongue.

Figure 12A:
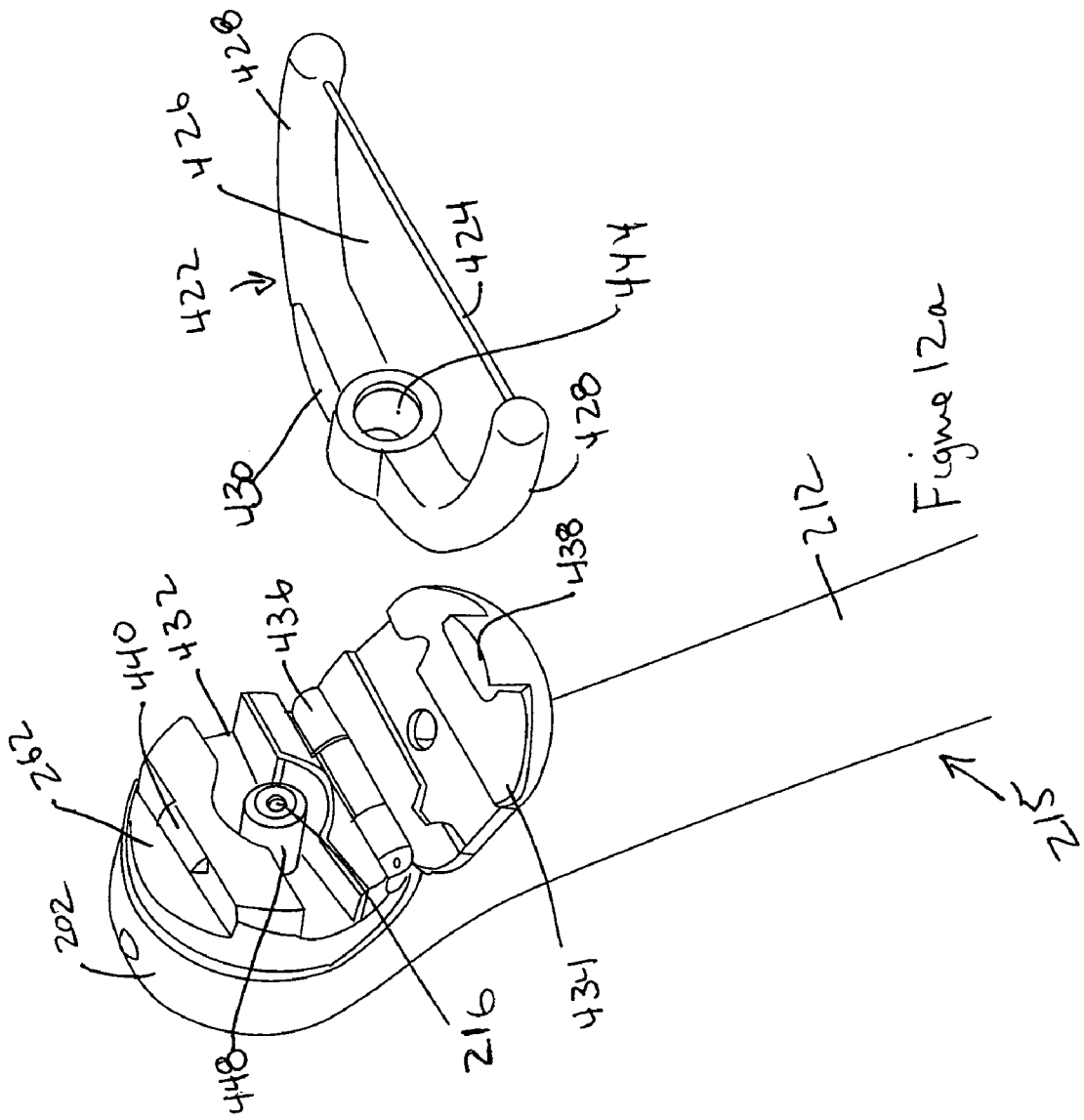
FIG. 12a is an expanded view of a flossing neck/head assembly shown in FIG. 11.
Figure 126:
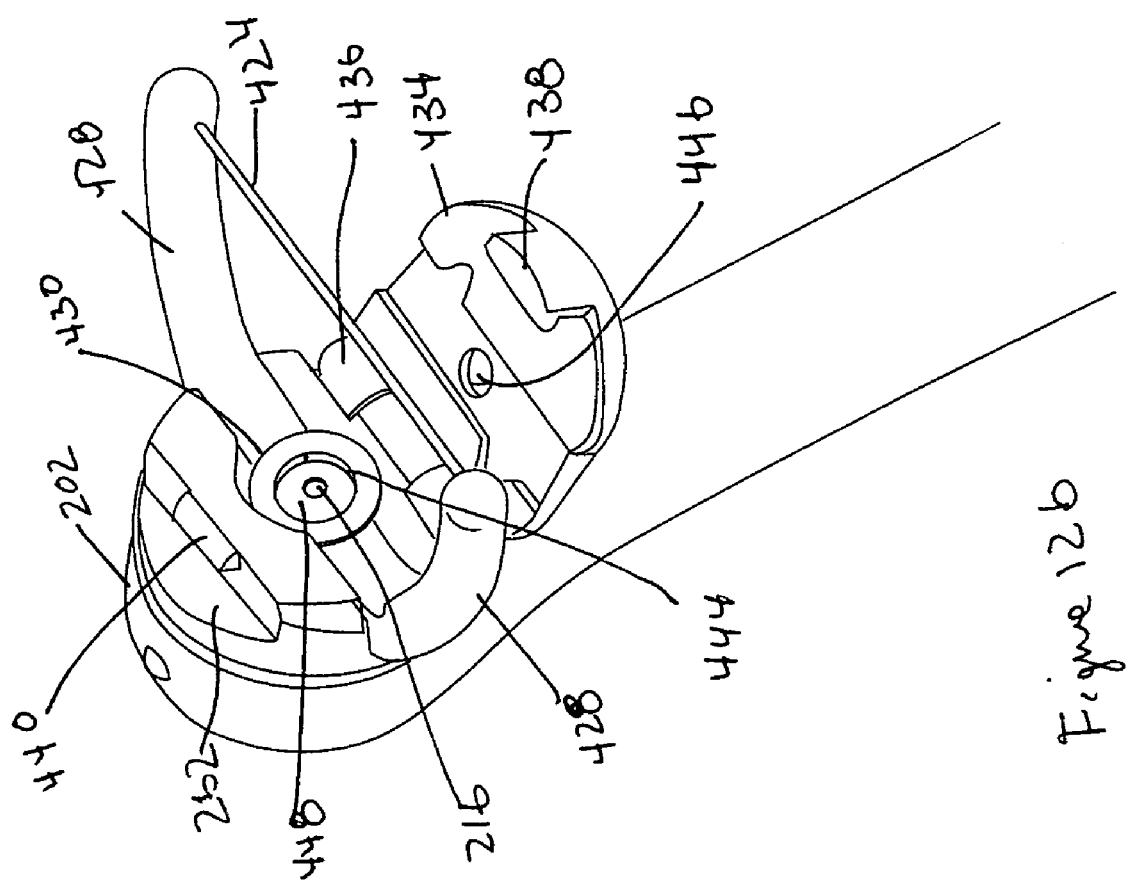

A fourth neck/head assembly 420 is also provided and shown with a flossing tool 422 (best illustrated in FIGS. 12a and 12b). The flossing tool 422 has a section of flossing material 424 suspended over a cavity 426 that is created between two opposable arms 428, which extend from a support region 430. The support region 430 fits into a channel 432 on the moveable section 262 of the head 202, thereby permitting a used flossing tool 422 to be replaceable. A locking cap 434 is also provided to hold the flossing tool 422 in place. The locking cap 434 is hinged 436 on one end to the moveable section 262 and includes a tab 438 that frictionally fits into a corresponding detent 440 on the opposite end of the moveable section 262.

To allow the pressurized liquid to flow from the head 202 of the device 200, the movable section 262, as mentioned above, includes a nozzle, aperture, or opening 216. The flossing tool 430 also includes an aperture 444 that aligns with the opening 216, when the flossing tool 430 is secured to the movable section 262. In addition, the cap 434 includes a cap opening 446 that similarly aligns with the opening 216 in the movable section 262 when the cap 434 is closed. The movable section 262 may also include a stem 448 extending from the channel 432. The stem 448 is bored therethrough to accommodate the opening 216. The stem 448 is sized to fit within the aperture 444 on the flossing tool 430. This helps to align the aperture 444 with the opening 216 and may also frictionally engage the flossing tool 430 to the movable section 262.

As explained above, the present invention includes the ability to jet out a pressurized fluid, not only inclusive of a liquid but also a gas. For example, the user may simply pump air into and pressurize the air inside the reservoir. Once the reservoir contains a sufficient amount of pressurized air, the user may release it by pressing the button. While not as efficient as expelling pressurized liquid, in some instances the liquid, especially an antiseptic liquid, may be too sensitive for the user. Moreover, if pressurized gas such as air was the only intentional use of the device, the pump does not have to be removable, as the user can continuously refill the reservoir with air without removing the pump.

From the foregoing and as mentioned above, it will be observed that numerous variations and modifications may be effected without departing from the spirit and scope of the novel concept of the invention covering a self-contained device incorporating a reservoir, an on-board pump, and a nozzle into a single device with interchangeable heads to provide various oral cleaning actions.

It is to be understood that no limitation with respect to the specific methods and apparatus illustrated herein is intended or inferred. It is intended to cover by the appended claims all such modifications as fall within the scope of the claims.

We claim:
1. An oral cleaning device comprising:
a refillable reservoir having an upper aperture;
a manual operable pump attached to the reservoir, the manual operation of said pump increases pressure within the reservoir such that a liquid contained in the reservoir becomes pressurized liquid;
a first mechanism in communication with the reservoir for controlling the flow of pressurized liquid from exiting the upper aperture of the reservoir, thereby controlling the flow of pressurized liquid out of the device;
a mid section attached between a neck portion and the reservoir;
a head attached to the neck portion and having an outlet for expelling pressurized liquid contained in the reservoir and further having a movable section rotatably connected thereto;
the movable section includes a flossing tool that includes flossing material supported about the outlet, a channel region and a stem extending from said channel region, the stem being bored therethrough to be in communication with the outlet of the head;
the flossing tool further includes a pair of arms extending from a center region to define a cavity therebetween, the pair of arms supporting the flossing material over said cavity, the center region having an opening, the center region being sized to fit within the channel region such that the opening in the center region aliens with the stem of the device;
a means of allowing pressurized liquid exiting the upper aperture to travel to the outlet in the head;
an electrically operated motor in said mid section;
a means interconnecting said motor and said movable section to move said movable section when said motor is operated; and
a second mechanism in communication with the motor for controlling the operation of the motor mechanism, thereby controlling the movement of the movable section.

2. The device of claim 1, wherein said neck portion having a first region designed to mate with a second region defined on the mid section, such that the neck portion and head attached thereto are removable from the device.

3. The device of claim 1, wherein the movable section includes a plurality of bristles.

4. The device of claim 1, wherein the movable section includes a soft tip nozzle.

5. The device of claim 1 further comprising: a cap hinged to said movable section, said cap and said movable section include a means to secure the cap in a closed position through said cavity of the flossing tool that is in engagement therewith, wherein said closed position prevents the flossing tool from separating from said movable section, the cap having a hole that when the cap is in said closed position moves into alignment with the opening in the center region on the flossing tool.

6. The device of claim 1, wherein the means of allowing pressurized liquid exiting the upper aperture to travel to the outlet in the head includes a tube secured from the upper aperture to the neck and a channel defined by the neck that is in communication with the tube and the upper aperture.

7. An oral cleaning device comprising:

a body portion having a neck and a head extending from one end of the body portion and having a refillable reservoir extending from another end of the body portion;

a manually operable means for pressurizing fluid contained in said reservoir;

a means for dispensing pressurized fluid contained in said reservoir out of an aperture defined by the head;

a means for mechanically oscillating a movable section rotatably secured to the head, wherein the movable section includes a flossing tool that includes flossing material supported about the outlet;

the movable section further includes a channel region and a stem extending from said channel region, the stem being bored therethrough to be in communication with the outlet of the head; and the flossing tool includes a pair of arms extending from a center region to define a cavity therebetween, the pair of arms supporting the flossing material over said cavity, the center region having an opening, the center region being sized to fit within the channel region such that the opening in the center region aligns with the stem of the device.

8. The device of claim 7, wherein the manually operable means for pressurizing fluid contained in said reservoir includes a pump cylinder with a one way valve operably connected to the reservoir, a pump piston slidably engaged within the pump cylinder.

9. The device of claim 7, wherein the means for dispensing pressurized fluid contained in said reservoir out of said aperture defined by the head includes a manual operable valve mechanism disposed between an opening in the reservoir and the aperture defined by the head.

10. The device of claim 7, wherein the means for mechanically oscillating the movable section rotatably secured to the head includes an electrically operated motor driving a transmission assembly that is connected to said movable section such that when said transmission assembly is being driven by said motor said movable section oscillates.

11. The device of claim 7, wherein the movable section includes a plurality of bristles.

12. The device of claim 7, wherein the movable section includes a soft tip nozzle.

13. The device of claim 7 further comprising: a cap hinged to said movable section, said cap and said movable section include a means to secure the cap in a closed position through said cavity of the flossing tool that is in engagement therewith, wherein said closed position prevents the flossing tool from separating from said movable section, the cap having a hole that when the cap is in said closed position moves into alignment with the opening in the center region on the flossing tool.

* * * * *